US010905485B2

(12) United States Patent
Giffard et al.

(10) Patent No.: US 10,905,485 B2
(45) Date of Patent: Feb. 2, 2021

(54) APPARATUS FOR MIXING BONE CEMENT

(71) Applicant: Zimmer Biomet France SAS, Brognard (FR)

(72) Inventors: Lenaic Giffard, Valence (FR); Alexis Dupuy, Valence (FR); Sebastien Chaligne, Brette les Pins (FR); Julie Mottet, Chabeuil (FR)

(73) Assignee: Zimmer Biomet France SAS, Brognard (FR)

( * ) Notice: Subject to any disclaimer, the term of this patent is extended or adjusted under 35 U.S.C. 154(b) by 126 days.

(21) Appl. No.: 15/660,177

(22) Filed: Jul. 26, 2017

(65) Prior Publication Data

US 2018/0028247 A1    Feb. 1, 2018

Related U.S. Application Data

(60) Provisional application No. 62/367,218, filed on Jul. 27, 2016.

(51) Int. Cl.
*A61B 17/88* (2006.01)
*B01F 11/00* (2006.01)
(Continued)

(52) U.S. Cl.
CPC ...... *A61B 17/8802* (2013.01); *A61B 17/8805* (2013.01); *A61B 17/8825* (2013.01);
(Continued)

(58) Field of Classification Search
CPC ........ A61B 2017/8838; A61B 17/8833; A61B 17/8802; B01F 2215/0029
See application file for complete search history.

(56) References Cited

U.S. PATENT DOCUMENTS 4,827,973 A    5/1989 Boehmer
4,861,335 A    8/1989 Reynolds
(Continued)

FOREIGN PATENT DOCUMENTS

CN    106321916 A    1/2017
CN    107289156 A    10/2017
(Continued)

OTHER PUBLICATIONS

"International Application Serial No. PCT EP2017 069093, International Preliminary Report on Patentability dated Feb. 7, 2019", 14 pgs.

(Continued)

*Primary Examiner* — Olivia C Chang
(74) *Attorney, Agent, or Firm* — Schwegman Lundberg & Woessner, P.A.

(57) ABSTRACT

An apparatus for mixing bone cement can comprise a receiving chamber, a mixing chamber, a cannula, a base, and a piston located within the mixing chamber. The receiving chamber defining a conduit. The mixing chamber in fluid communication with the receiving chamber. The mixing chamber configured to house a first component of the bone cement. The cannula located in the receiving chamber and in fluid communication with the conduit. The base including a bladder arranged to be punctured by the cannula, the bladder configured to house a second component of the bone cement. Upon puncturing of the bladder by the cannula the second component of the bone cement passes through the conduit and the cannula into the mixing chamber. The piston configured to seal the mixing chamber upon movement of the piston from a first position relative to the conduit to a second position relative to the conduit.

19 Claims, 17 Drawing Sheets

(51) Int. Cl.
  *B01F 15/02* (2006.01)
  *B01F 15/00* (2006.01)
(52) U.S. Cl.
  CPC ...... *A61B 17/8827* (2013.01); *A61B 17/8833* (2013.01); *B01F 11/0054* (2013.01); *B01F 15/00506* (2013.01); *B01F 15/0206* (2013.01); *B01F 15/0223* (2013.01); *A61B 2017/8838* (2013.01); *B01F 2215/0029* (2013.01)

(56) References Cited

U.S. PATENT DOCUMENTS

| | | | |
|---|---|---|---|
| 5,067,948 A | 11/1991 | Haber et al. | |
| 7,018,089 B2* | 3/2006 | Wenz | A61M 5/31511 206/219 |
| 2006/0184137 A1 | 8/2006 | Reynolds | |
| 2006/0274601 A1 | 12/2006 | Seaton, Jr. | |
| 2014/0192611 A1* | 7/2014 | Sasaki | B01F 15/0206 366/139 |
| 2015/0103616 A1* | 4/2015 | Giffard | B01F 15/0226 366/76.93 |
| 2016/0038209 A1* | 2/2016 | Grebius | B01F 15/0258 606/93 |
| 2016/0045242 A1 | 2/2016 | Bielenstein et al. | |
| 2017/0120037 A1 | 5/2017 | Thorne | |
| 2019/0314075 A1 | 10/2019 | Dupuy et al. | |

FOREIGN PATENT DOCUMENTS

| | | |
|---|---|---|
| CN | 109789382 A | 5/2019 |
| DE | 4425218 | 1/1996 |
| DE | 10302488 A1 | 1/2005 |
| EP | 0727531 A1 | 8/1996 |
| JP | 09510659 A | 10/1997 |
| JP | 2001104482 | 4/2001 |
| JP | 2019524261 A | 9/2019 |
| WO | 2004026377 | 4/2004 |
| WO | WO-2006118748 A1 | 11/2006 |
| WO | 2008022481 | 2/2008 |
| WO | 2018019967 A2 | 2/2018 |

OTHER PUBLICATIONS

"International Application Serial No. PCT/EP2017/069093, International Search Report dated Jan. 29, 2018", 7 pgs.

"International Application Serial No. PCT/EP2017/069093, Written Opinion dated Jan. 29, 2018", 12 pgs.

"International Application Serial No. PCT/EP2017/069093, Invitation to Pay Add'l Fees and Partial Search Rpt dated Nov. 28, 2017", 15 pgs.

"European Application Serial No. 17748451.6, Communication Pursuant to Article 94(3) EPC dated Apr. 3, 2020", 5 pgs.

"European Application Serial No. 19168224.4, Extended European Search Report dated Mar. 12, 2020", 9 pgs.

"Japanese Application Serial No. 2019-504038, Notification of Reasons for Refusal dated Mar. 10, 2020", (W/ English Translation), 9 pgs.

"Japanese Application Serial No. 2019-504038, Response filed Jun. 10, 2020 to Notification of Reasons for Refusal dated Mar. 10, 2020", with English claims, 18 pages.

"European Application Serial No. 17748451.6, Response filed Aug. 13, 2020 to Communication Pursuant to Article 94(3) EPC dated Apr. 3, 2020", 12 pages.

"European Application Serial No. 17748451.6, Response to Communication pursuant to Rules 161(1) and 162 EPC filed Sep. 23, 2019", 17 pgs.

"European Application Serial No. 19168224.4, Response filed Oct. 15, 2020 to Extended European Search Report dated Mar. 12, 2020", 10 pgs.

* cited by examiner

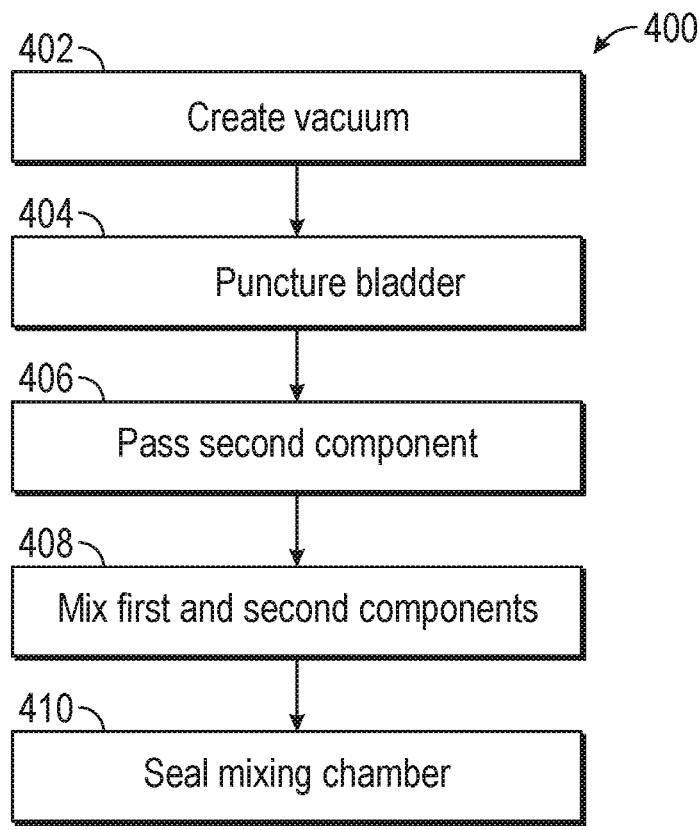
FIG. 4
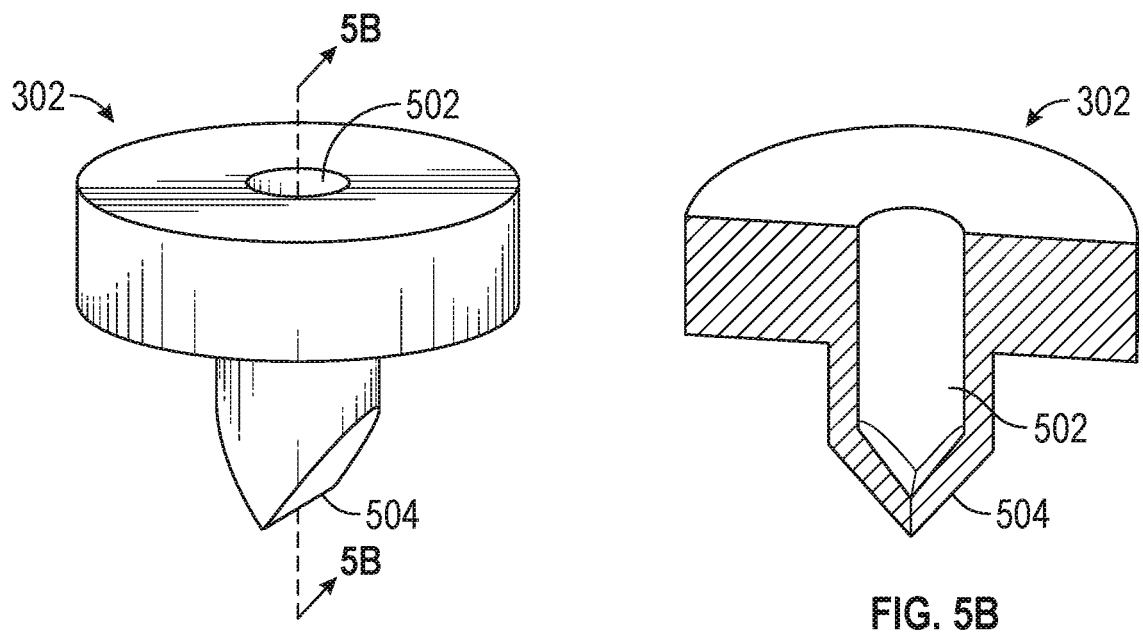
FIG. 5A
FIG. 5B

APPARATUS FOR MIXING BONE CEMENT

PRIORITY CLAIM

This application claims priority to U.S. Provisional Application No. 62/367,218, filed on Jul. 27, 2016, the contents of which are hereby incorporated in its entirety.

FIELD OF THE DISCLOSURE

The present disclosure relates to surgical implant systems, including instruments and methods for mixing bone cement.

BACKGROUND

Bone cement is a substance that can be used by surgeons to anchor or help anchor components of an implant or fuse bone. For example, bone cement can be used to secure components, such as knee components, hip components, etc. to existing bone during joint replacement procedures. Bone cement also can be used to fuse bones, such as vertebra.

SUMMARY

To better illustrate the system disclosed herein, a non-limiting list of examples is provided here:

Example 1 can include an apparatus for mixing bone cement. The apparatus can comprise a receiving chamber, a mixing chamber, a cannula, a base, and a piston. The receiving chamber can define a conduit. The mixing chamber can be in fluid communication with the receiving chamber. The mixing chamber can be configured to house a first component of the bone cement. The cannula can be located in the receiving chamber and can be in fluid communication with the conduit. The base can include a bladder arranged to be punctured by the cannula. The bladder can be configured to house a second component of the bone cement. Upon puncturing of the bladder by the cannula, the second component of the bone cement can pass through the conduit and the cannula into the mixing chamber. The piston can be located within the mixing chamber. The piston can be configured to seal the mixing chamber upon movement of the piston from a first position relative to the conduit to a second position relative to the conduit.

In Example 2, the apparatus of Example 1 can optionally include a valve in fluid communication with the conduit. The movement of the piston from the first position to the second position can cause the valve to close.

In Example 3, the apparatus of Example 2 can optionally include the valve comprising a duck valve. When the piston is in the first position a portion of the duck valve surrounds a portion of the conduit.

In Example 4, the apparatus of any one of or any combination of Examples 1-3 can optionally include a safety strip connected to the base. The safety strip can be configured to prevent the bladder from being punctured by the cannula until the safety strip is removed from the base.

In Example 5, the apparatus of any one of or any combination of Examples 1-4 can optionally include the base being configured to move relative to the mixing chamber co-axially.

In Example 6, the apparatus of any one of or any combination of Examples 1-5 can optionally include the second component comprising a liquid.

In Example 7, the apparatus of any one of or any combination of Examples 1-5 can optionally include the second component comprising a monomer.

In Example 8, the apparatus of any one of or any combination of Examples 1-7 can optionally include the first component comprising a powder.

In Example 9, the apparatus of any one of or any combination of Examples 1-8 can optionally include a filter connected to the piston and configured to prevent the first component from entering the valve assembly and the bladder upon puncturing of the bladder.

In Example 10, the apparatus of any one of or any combination of Examples 1-9 can optionally include the bladder including a flexible membrane configured to decrease in volume upon puncturing of the bladder.

In Example 11, the apparatus of any one of or any combination of Examples 1-10 can optionally include the base including a second cannula and a second bladder. The second cannula can be arranged to puncture the second bladder.

In Example, 12, the apparatus of any one of or any combination of Examples 1-11 can optionally include the base further including a flexible tab. When the flexible tab is in a first position, the base can be secured to the mixing chamber in a fixed position. When the flexible tab is in a second position, the base can be free to move along a longitudinal axis of the mixing chamber.

In Example 13, the apparatus of any one of or any combination of Examples 1-12 can optionally include a handle. The handle can include a cannulate component, a rod sized to pass through the cannulated component, and a mixing head attached to the cannulated component. When the rod is removed from the cannulated component, the mixing head can be detachable from the cannulated component.

In Example 14, the apparatus of any one of or any combination of Examples 1-13 can optionally include the bladder being completely located within the base.

In Example 15, the apparatus of any one of or any combination of Examples 1-13 can optionally include a first portion of the bladder being located within an interior cavity defined by the base and a second portion of the bladder being located proximate an exterior of the base.

Example 16 can include an apparatus for mixing bone cement. The apparatus can comprise a mixing chamber, a receiving chamber, a cannula, a base, and a piston. The mixing chamber can be configured to house a first component of the bone cement. The receiving chamber can define a conduit configured to fluidly connect the mixing chamber and the receiving chamber. The cannula can be located within the receiving chamber and in fluid communication with the conduit. The base can include a bladder configured to house a second component of the bone cement. A portion of the base can be sized to be received within the receiving chamber such that upon a relative movement between the base and the receiving chamber, the bladder is punctured by the cannula. The piston can be located within the mixing chamber and configured to engage the receiving chamber. The piston can include a valve configured to allow the second component of the bone cement to pass through the cannula from the bladder into the mixing chamber and seal the mixing chamber upon disengagement of the receiving chamber from the piston.

In Example 17, the apparatus of Example 16 can optionally include the valve being a duck valve.

In Example 18, the apparatus of any one of or any combination of Examples 16 and 17 can optionally include a filter connected to the piston and configured to prevent the first component from entering the valve assembly and the bladder upon the bladder being punctured by the cannula.

In Example 19, the apparatus of any one of or any combination of Examples 16-18 can optionally include a safety strip connected to the body. The safety strip can be configured to prevent the bladder from being punctured by the cannula.

In Example 20, the apparatus of any one of or any combination of Examples 16-19 can optionally include the first component comprising a powder and the second component comprises a monomer.

In Example 21, the apparatus of any one of or any combination of Examples 16-20 can optionally include the relative movement between the base and the receiving chamber including the base being configured to move co-axially relative to the mixing chamber.

Example 22 can include a method of mixing bone cement. The method can comprise puncturing a bladder with a cannula connected to a receiving chamber, the receiving chamber in fluid communication with a mixing chamber, the mixing chamber including a first component of the bone cement, the bladder including a second component of the bone cement; causing the second component of the bone cement to pass through the cannula from the bladder into the mixing chamber; and mixing the first component of the bone cement with the second component of the bone cement within the mixing chamber.

In Example 23, the method of Example 22 can optionally include moving a piston located within the mixing chamber, wherein moving the piston causes a valve connected to a conduit defined by the receiving chamber to close, thereby preventing the bone cement from passing through the conduit.

In Example 24, the method of any one of or any combination of Examples 22 and 23 can optionally include disengaging the receiving chamber from the piston.

In Example 25, the method of any one of or any combination of Examples 22-24 can optionally include creating a vacuum within the mixing chamber prior to puncturing the bladder with the cannula.

Example 26 can include an apparatus for mixing bone cement. The apparatus can include a mixing chamber, a base, a piston, a cap, and a mixing handle. The mixing chamber can have a first end and a second end. The mixing chamber can be configured to house a first component and a second component of the bone cement. The base can be located proximate the first end of the mixing chamber. The piston can be located within the mixing chamber and connected to the base. The piston can be configured to move co-axially from a first position to a second position upon separation of the base from the mixing chamber. The cap can be connected to the second end of the mixing chamber. The mixing handle can pass through the cap. The mixing handle can comprise a cannulate component, a rod sized to pass through the cannulated component, and a mixing head attached to the cannulated component. When the rod is removed from the cannulated component, the mixing head can be detachable from the cannulated component.

In Example 27, the apparatus of Example 26 can optionally include the base being connected to the piston via a threaded connection.

In Example 28, the apparatus of any one of or any combination of Examples 26 and 27 can optionally include the cannulation component including a plurality of flexible tabs configured to engage the mixing head.

In Example 29, the apparatus of any one of or any combination of Examples 26-28 can optionally include the cap defining a vacuum port.

In Example 30, the apparatuses or methods of any one of or any combination of Examples 1-29 is optionally configured such that all elements or options recited are available to use or select from.

BRIEF DESCRIPTION OF THE FIGURES

The above-mentioned and other features and advantages of this disclosure, and the manner of attaining them, will become more apparent and the disclosure itself will be better understood by reference to the following description of embodiments taken in conjunction with the accompanying drawings, wherein:

FIG. 4 shows an example method for mixing bone cement in accordance with at least one example of the present disclosure.

FIGS. 5A and 5B show an example valve in accordance with at least one example of the present disclosure.

Corresponding reference characters indicate corresponding parts throughout the several views. The exemplifications set out herein illustrate exemplary embodiments of the disclosure, and such exemplifications are not to be construed as limiting the scope of the disclosure any manner.

DETAILED DESCRIPTION

As used herein, the following directional definitions apply. Anterior and posterior mean nearer the front or nearer the rear of the body, respectively, proximal and distal mean nearer to or further from the root of a structure, respectively, and medial and lateral mean nearer the sagittal plane or further from the sagittal plane, respectively. The sagittal plane is an imaginary vertical plane through the middle of the body that divides the body into right and left halves. In addition, the terms implant and prosthesis, and variations thereof, can be used interchangeably.

Bone cement can be a multicomponent substance and each of the components can be mixed at a time of use. For example, during a hip arthroplasty a surgeon can mix bone cement components as needed to secure implant components, such as a femoral component or an acetabular component. The bone cement components can be contained in a single apparatus or system. For example, a first component, such as a powder or other solid bone cement component, can be stored in a mixing chamber and a second component, such as a liquid or monomer, can be stored in a bladder.

To mix the first component and the second component of the bone cement, a base, which can include the bladder, can be inserted into a receiving chamber of the system or apparatus. Upon making a relative movement between the base and the receiving chamber, a cannula can puncture the bladder. A vacuum created in the mixing chamber prior to making the relative movement between the mixing chamber and the receiving chamber can cause the second component to flow into the mixing chamber upon puncturing of the bladder.

A piston can be located within the mixing chamber. The base can define a conduit sized to receive the cannula such that the second component can pass through the cannula and the conduit into the mixing chamber upon puncturing of the bladder by the cannula. A valve, such as a duck valve, can be in fluid communication with the conduit and can seal the connection between the mixing chamber and the receiving chamber conduit, in order the allow the second component free flowing into the mixing chamber thanks to pressure gradient.

After the first and second bone cement components have entered the mixing chamber, the base or, the receiving chamber including the base, can be removed and the valve can seal the first and second bone cement components in the mixing chamber. A handle passing through a top of the mixing chamber can be connected to a mixer. Articulation of the handle can cause movement of the mixer and the mixing of the bone cement components. The piston can pass from the first position to a second position thanks to the sealing by the valve. To deliver the bone cement, the cap or handle can be removed from the mixing chamber and the mixing chamber can be connected to an applicator for delivery by the surgeon.

Figure 1:
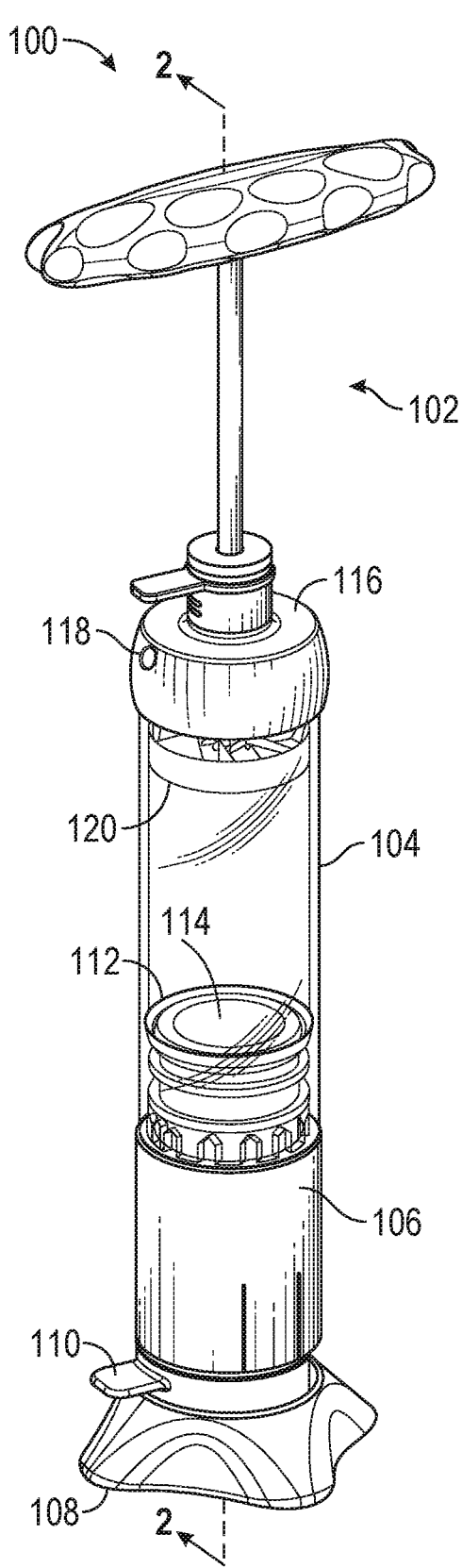
FIG. 1 shows an example of a system for mixing bone cement in accordance with at least one example of the present disclosure.

Turning now to the figures, FIG. 1 shows an apparatus 100 for mixing bone cement in accordance with at least one example of the present disclosure. As shown in FIG. 1, the apparatus 100 can include a handle 102, a mixing chamber 104, a receiving chamber 106, a base 108, and a safety strip 110. A piston 112 can be located within the mixing chamber 104 and a filter 114 can be located on top of the piston 112. The handle 102 can pass through a cap 116 that can seal a portion of the mixing chamber 104. As discussed herein, the cap 116 can include a vacuum port 118 that can be used to connect the apparatus 100 to a vacuum pump (not shown) to create a vacuum within the mixing chamber 104.

The handle 102 can be connected to a mixer 120. After bone cement components have been introduced into the mixing chamber 104, the handle 102 can be articulated such that the mixer 120 moves along a longitudinal axis of the mixing chamber 104. The movement of the mixer 120 can allow the bone cement components to be mixed such that a homogenous mixture is created.

The walls defining the mixing chamber 104 can be opaque or transparent. Transparent walls, such as shown in FIG. 1 can allow the surgeon to view the bone cement during a mixing process. By allowing the surgeon to view the bone cement, the surgeon can determine when the bone cement components have been thoroughly mixed. In addition, the surgeon can determine an amount of bone cement remaining in the mixing chamber 104. For example, once the mixing chamber 104 has been transferred to an applicator (not shown), the surgeon can utilize a transparent mixing chamber 104 to determine if he or she has enough bone cement for a procedure to be undertaken. For instance, after installing a tibial component of a knee implant, the surgeon can view a remaining amount of bone cement in the mixing chamber 104 to determine if he or she has enough bone cement remaining to install a femoral component of the knee implant or if more bone cement needs to be mixed.

Figure 2:
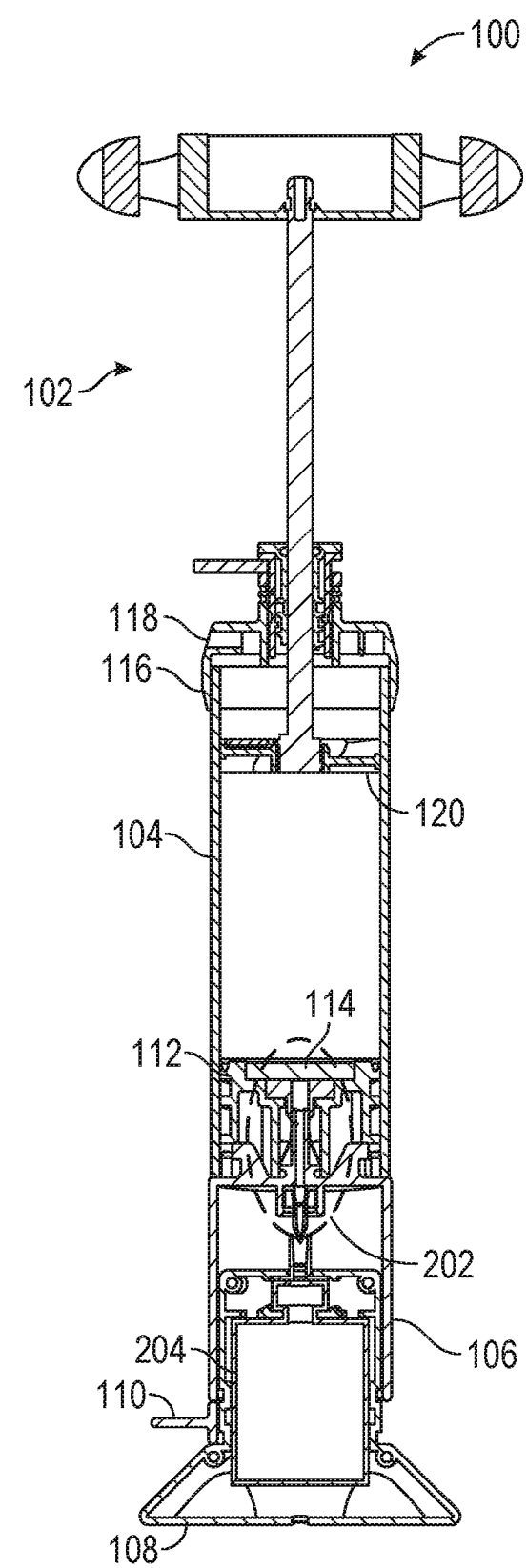
FIG. 2 shows an example of a cross-section of the system for mixing bone cement in accordance with at least one example of the present disclosure.
Figure 3A:
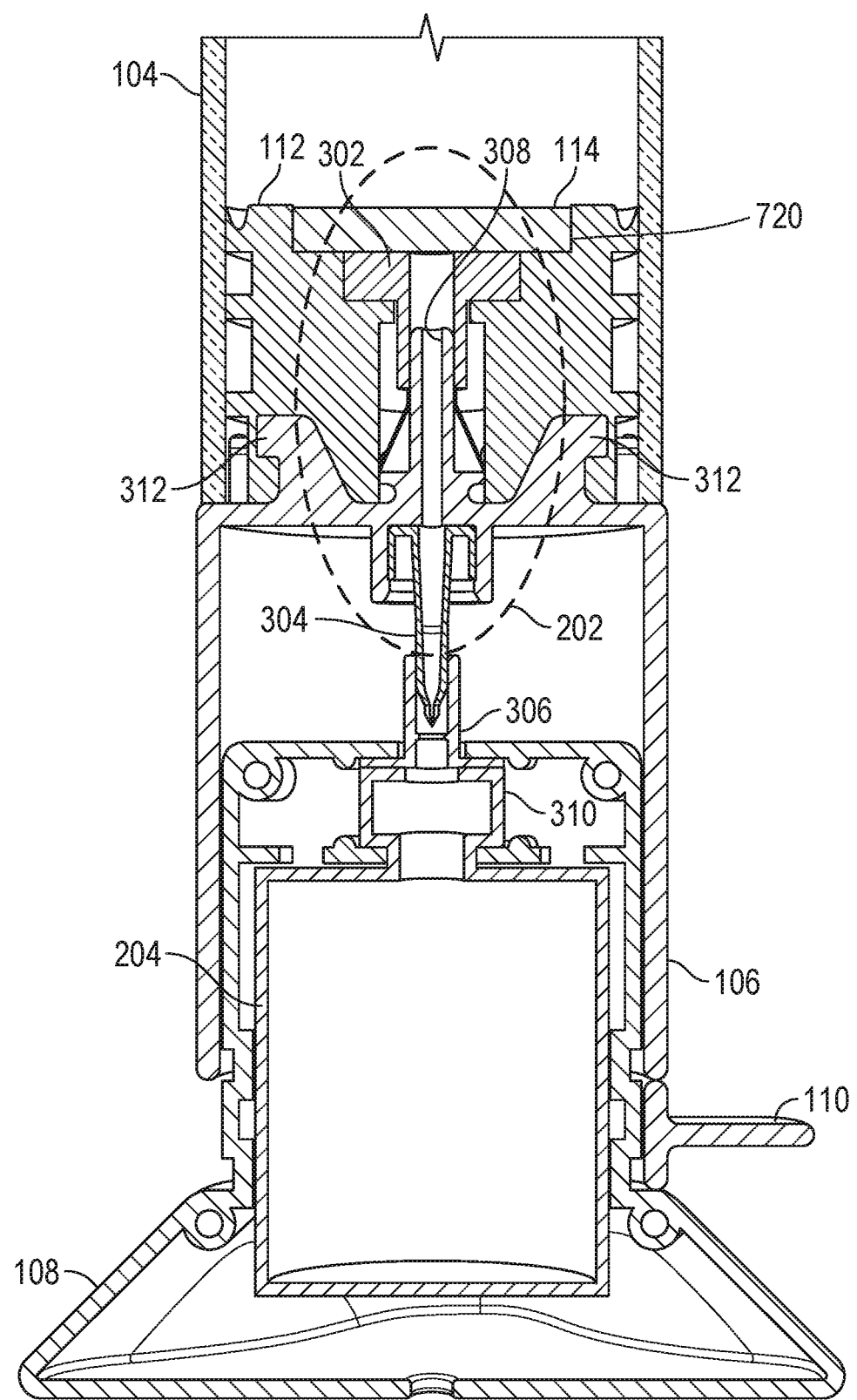
FIGS. 3A-3C show an example illustration of a method for transferring a liquid in accordance with at least one example of the present disclosure.
Figure 3B:
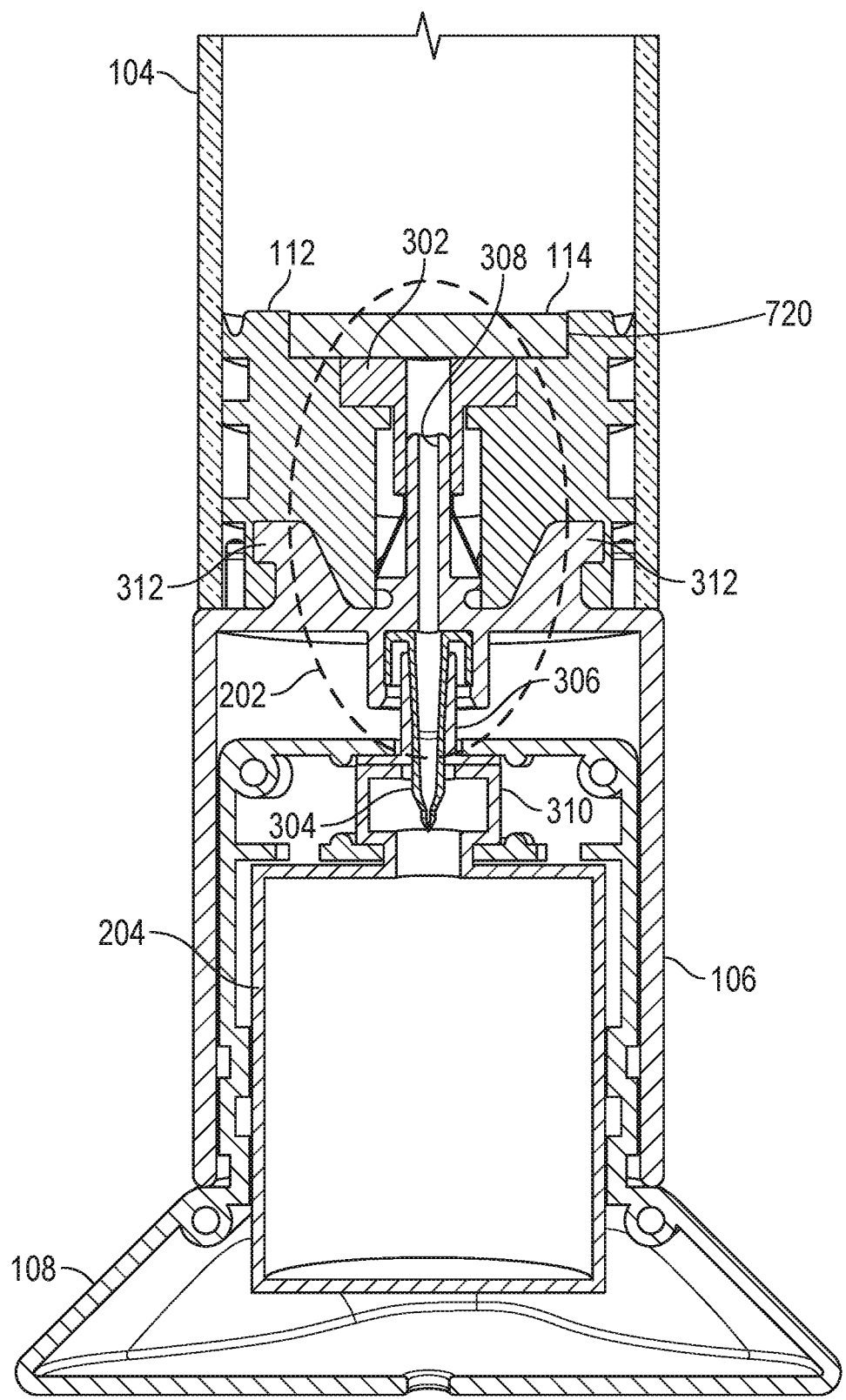
Figure 3C:
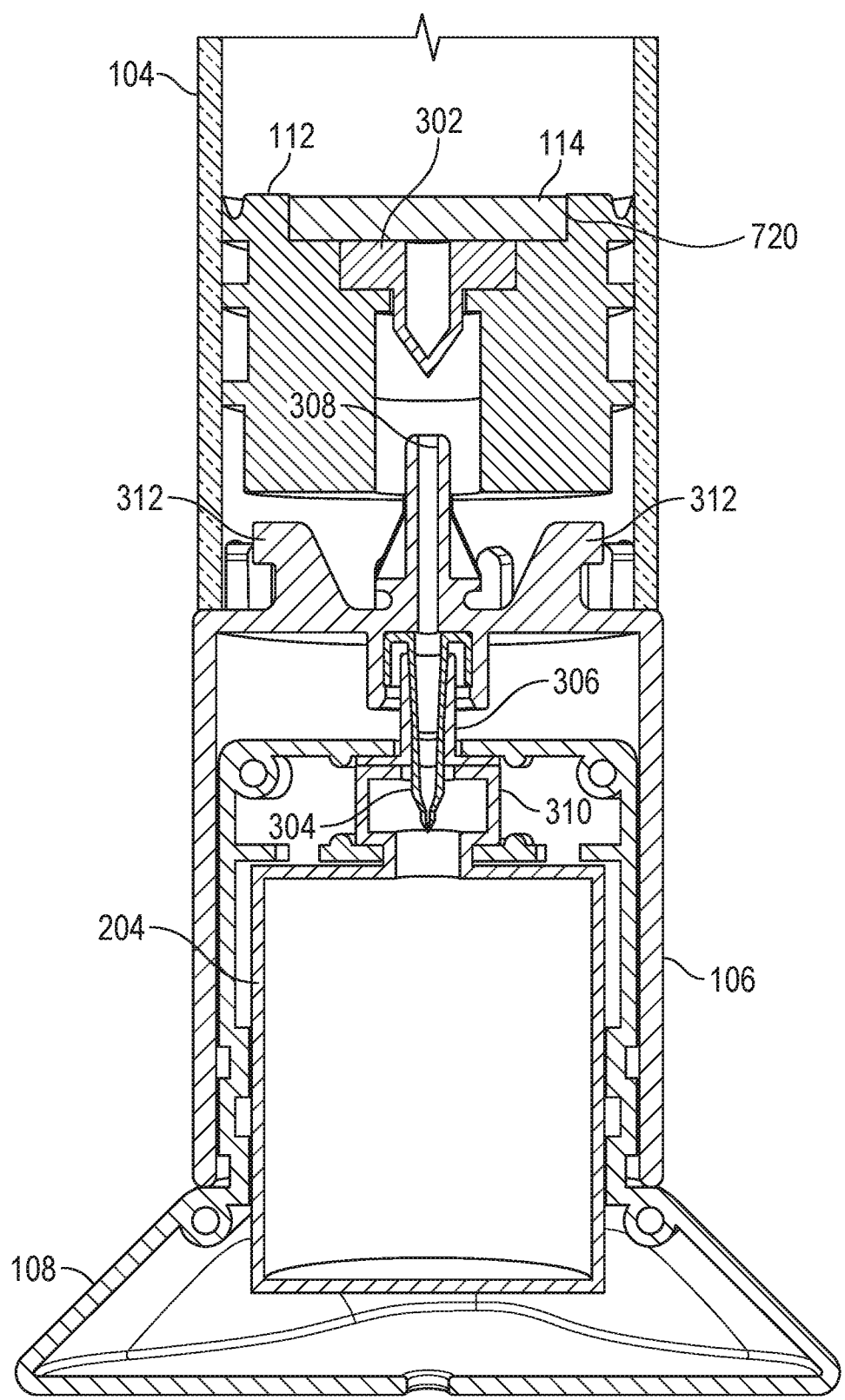

FIG. 2 shows a cross section of the apparatus 100 in accordance with at least one example of the present disclosure. As shown in FIG. 2, the apparatus 100 can include a valve assembly 202. In addition, a bladder 204 can be located in the base 108. FIGS. 3A-3C show the valve assembly 202 in accordance with at least one example of the present disclosure in greater detail. As shown in FIGS. 3A-3C, the valve assembly 202 can include the piston 112, the filter 114, a valve 302, a cannula 304, and a seal 306. The receiving chamber 106 can define a conduit 308 that can allow fluid communication between an interior portion of the receiving chamber 106 and the mixing chamber 104.

As shown in FIGS. 1-3C, the apparatus 100 can be shipped with the base 108 partially inserted within the receiving chamber 106. The safety strip 110 can hinder movement of the base 108 relative to the receiving chamber 106. FIGS. 3A-3C show example stages for using the apparatus 100 to mix bone cement. FIGS. 3A-3C will be discussed in conjunction with FIG. 4, which shows an example method 400 for mixing bone cement in accordance with at least one example of the present disclosure.

The method 400 can begin at stage 402 where a vacuum can be created within the mixing chamber 104 and the valve assembly 202. As indicated above, the vacuum port 118 can be connected to a vacuum pump (not shown) in order to create a vacuum within the mixing chamber 104. The vacuum pump can be a hand operated pump or an electric pump.

From stage 402, the method 400 can proceed to stage 404 where bladder 204 can be punctured. The bladder 204 can be punctured by the cannula 304. As indicated above, the base 108 can be partially inserted into the receiving chamber 106 by a manufacturer. The safety strip 110 can be used to prevent the base 108 from advancing further into the receiving chamber 106 during transport. As a result, puncturing the bladder 204 can also include removing the safety strip 110. As shown in FIG. 3B, the base 108 can be moved co-axially relative to the receiving chamber 106, which can cause the cannula 304 to puncture both the seal 306 and the bladder 204.

From stage 404, the method 400 can proceed to stage 406 where the second component of the bone cement can be caused to pass from the bladder 204 into the mixing chamber 104. For example, upon puncturing of the bladder, the vacuum created in the mixing chamber 104 and the valve assembly 202 can draw the second component located in the bladder 204 into the mixing chamber 104. For instance, the second component located in the bladder 204 can be a liquid monomer used as a curing agent or an epoxy for binding the first component of the bone cement already located within the mixing chamber 104. The pressure difference created by the vacuum can cause the second component to flow from the bladder 204 through the seal 306, the cannula 304, and the conduit 308 into the mixing chamber 104. To facilitate fluid flow, the bladder 204 can be a flexible or otherwise deformable structure. For example, the bladder 204 can be a flexible pouch that includes a head 310 for securing the bladder 204 to the base 108 as described below with respect to FIG. 8. Once the bladder 204 is punctured, the volume of the bladder 204 can decrease as the second component of the bone cement is drawn into the mixing chamber 104.

From stage 406, the method 400 can proceed to stage 408 where the first component of the bone cement and the second component of the bone cement can be mixed within the mixing chamber 104. As indicated above, the handle 102 can be articulated to cause movement of the mixer 120 to mix the first component and the second component. In addition, the mixing chamber 104 could be agitated to mix the first component and the second component.

From stage 408, the method 400 can proceed to stage 410 where the mixing chamber 104 can be sealed. As shown in FIG. 3C, the piston 112 can be moved away from the base 108 or, the receiving chamber 106 including the base 108. The movement of the piston 112 can cause the valve 302 to close such that the piston can now pass from a first position to a second position. The filter 114 can prevent the first component of the bone cement from exiting the mixing chamber 104 through the piston 112. The movement of the piston 112 can be caused by the vacuum created within the mixing chamber 104 or by removing the base 108 from the receiving chamber 106. For example, as discussed below, the piston 112 can be secured to the base 108 and removing the base 108 from the receiving chamber 106 can allow the piston to move due to the vacuum created within the mixing chamber 104 or by an external force applied by the surgeon. The movement of the piston 112 can cause the valve 302 to close, thereby sealing the piston 112 and the mixing chamber 104.

The valve 302 can be a duck valve. As shown in FIGS. 5A and 5B, the valve 302 can include a passage 502 that can allow fluid to flow through the valve 302. The valve 302 can also include a gate 504 that is reliant and naturally rests in a closed position as shown in FIGS. 5A and 5B. As shown in FIGS. 3A and 3B, the gate 504 can surround the conduit 308 in order to hold the valve 302 open. As the piston 112 is moved away from the conduit 308, the gate 504 can be removed from the conduit 308 and revert to a closed position.

Figure 6:
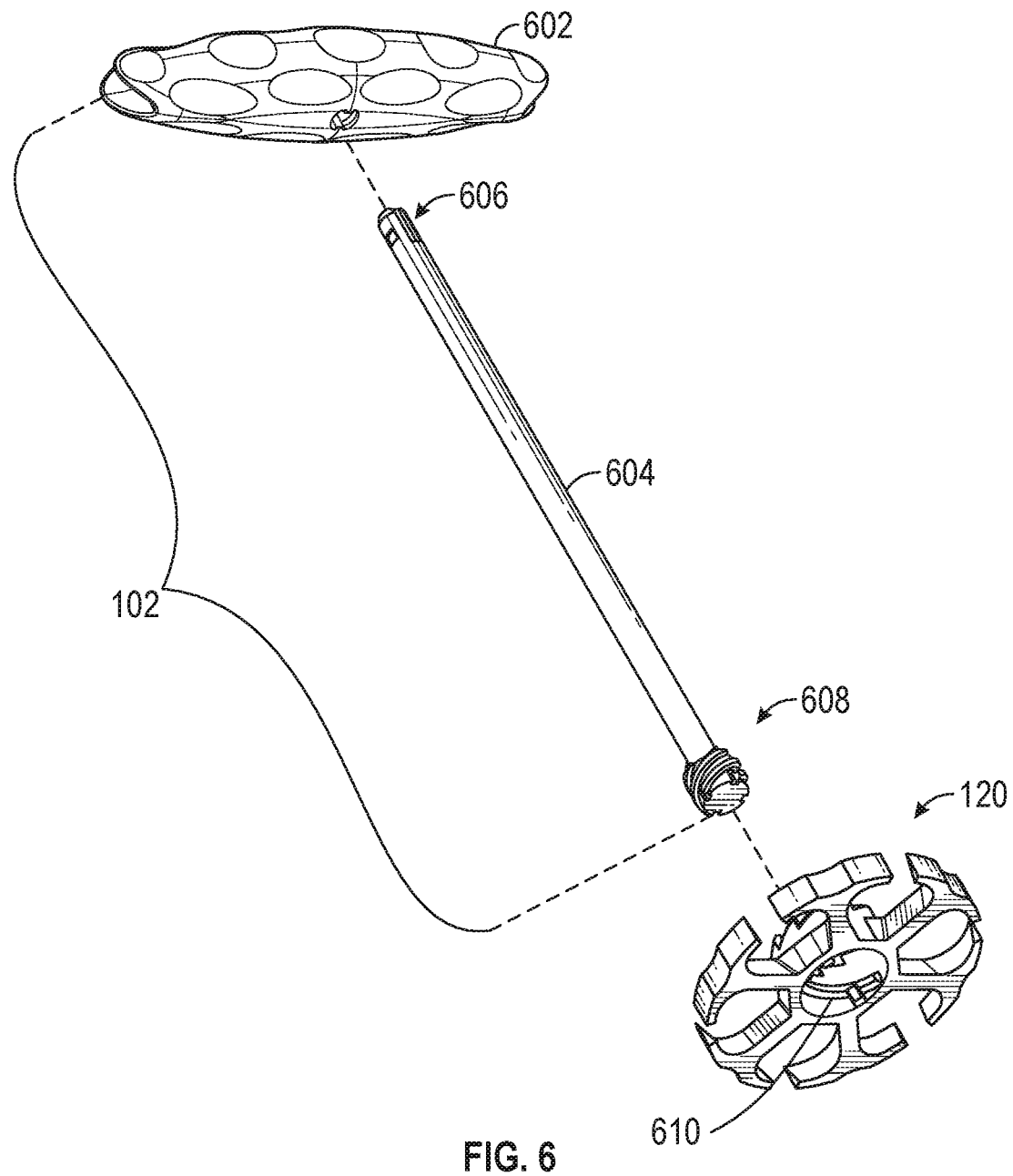
FIG. 6 shows an example exploded assembly of a handle and a mixer in accordance with at least one example of the present disclosure.

FIG. 6 shows an example exploded assembly of the handle 102 and the mixer 120. As shown in FIG. 6, the handle can include a grip 602 and a rod 604. The rod 604 can include one or more grooves 606 that can receive one or more nerves (not shown) located within the grip 602. The rod 604 can also include helical grooves 608. The mixer 120 can include complementary helical grooves 610. The helical grooves 608 can allow the rod 604 to mate with the mixer 120 via the complementary helical grooves 610.

The grip 602, the rod 604, and the mixer 120 can be manufactured from polymers, metals, ceramics, or combinations thereof. For example, the grip 602 can be manufactured from a polymer and the rod 604 and the mixer 120 can be manufactured from surgical grade stainless steel or titanium. The grip 602, the rod 604, and the mixer 120 can be manufactured from a variety of manufacturing techniques that include, but are not limited to, injection molding, over molding, machining, casting etc. For example, the rod 604 and the mixer 120 can each be machined using a computer numerical controlled (CNC) mill and the grip 602 can be injection molded. The rod 604 can be press fit into the grip 602.

Figure 7:
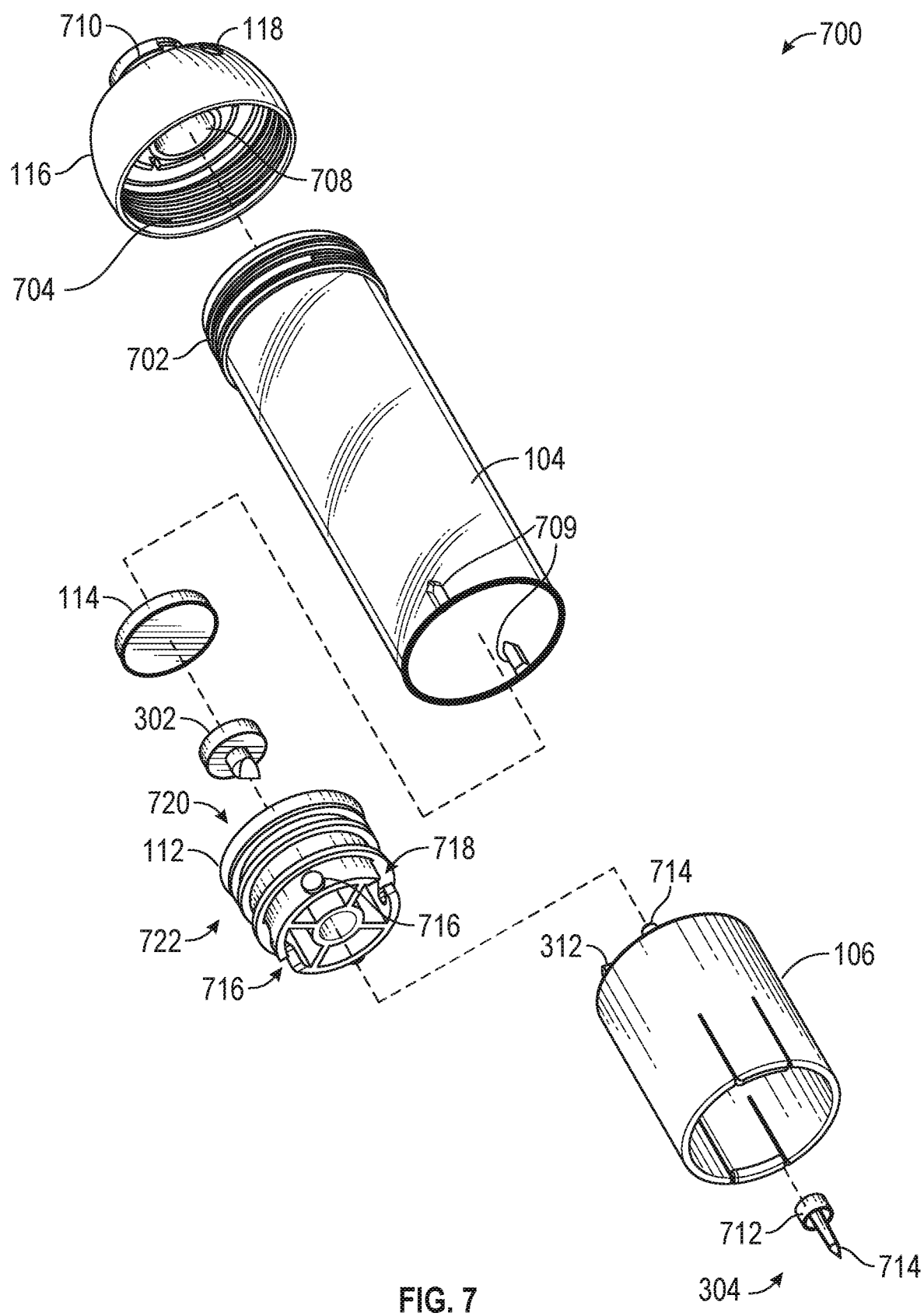
FIG. 7 shows an example exploded assembly of a body in accordance with at least one example of the present disclosure.

FIG. 7 shows an example exploded assembly of a body 700. The body 700 can include the cap 116, the mixing chamber 104, the piston 112, and the receiving chamber 106. As shown in FIG. 7, the mixing chamber 104 can include threads 702 located at a first end of the mixing chamber 104. The threads 702 can cooperate with threads 704 located on the cap 116 such that the cap 116 can be screwed to the mixing chamber 104. The mixing chamber 104 can also include ribs 706. As described herein, the ribs 706 can be used to secure and rotate the piston 112 via the receiving chamber 106 and for mounting the mixing chamber 104 to an applicator (not shown).

As discussed above, the mixing chamber 104 can be opaque or transparent. The mixing 104 chamber can be manufactured from polymers, metals, ceramics, or a combination thereof. For example, the mixing chamber 104 can be manufactured from a biocompatible polymer or metal. For instance, the mixing chamber 104 can be manufactured from titanium such that the mixing chamber 104 can be sterilized for use with multiple patients. In addition, the mixing chamber 104 can be manufactured from a variety of manufacturing techniques including, but not limited to, machining, injection molding, etc. For example, the mixing chamber 104 can be injection molded from a transparent polymer.

The cap 116 can define a through hole 708 that can allow the mixed bone cement to exit the mixing chamber 104. The cap 116 can also include threads 710. The threads 710 can allow a nozzle (not shown) to be connected to the cap 116. The nozzle can be used by the surgeon to direct the bone cement.

The cap 116 can also define the vacuum port 118. As discussed above, the vacuum port 118 can allow a vacuum pump to be connected to the cap 116. By connecting the vacuum pump to the vacuum port 118, a vacuum can be created within the mixing chamber 104 and the valve assembly 202.

The cap 116 can be manufactured from polymers, metals, ceramics, or a combination thereof. For example, the cap 116 can be manufactured from a biocompatible polymer or metal. For instance, the cap 116 can be manufactured from titanium such that the cap 116 can be sterilized for use with multiple patients. In addition, the cap 116 can be manufactured from a variety of manufacturing techniques including, but not limited to, machining, injection molding, etc. For example, the cap 116 can be injection molded from a polymer.

The cannula 304 can include a collar 712 and a tip 714. As shown in FIGS. 3A-3C, the collar 712 can fit into a recess formed in the receiving chamber 106. The cannula 304 can be press fit into the receiving chamber 106. The tip 714 can be sharp such that the tip 714 can puncture the bladder 204 when the base 108 is inserted into the receiving chamber 106.

The cannula 304 can be manufactured from metals, polymers, ceramics, or combinations thereof. The cannula 304 can be manufactured from a variety of manufacturing techniques including, but not limited to, stamping, machining, and injection molding.

As shown in FIGS. 3A-3C, the receiving chamber 106 can include one or more protrusions 312. The protrusions 312 can engage the piston 112 located in the mixing chamber 104. In addition, as discussed below, the protrusions 312 can allow for the piston 112 to be attached to the receiving chamber 106. As discussed herein, the receiving chamber can include the conduit 308. The conduit 308 can allow the second component in the bladder to flow through the piston 112 and into the mixing chamber 104.

The receiving chamber 106 can be manufactured from metals, polymers, ceramics, or combinations thereof. The receiving chamber 106 can be manufactured from a variety of manufacturing techniques including, but not limited to, stamping, machining, and injection molding, etc.

The piston 112 can include notches 718. The notches 718 can engage the protrusions 312 of the receiving chamber 106. Connecting the piston 112 to the receiving chamber 106 can prevent the piston 112 from moving while the apparatus 100 is in transport or while the vacuum is created in the mixing chamber 104. The piston 112 can also include a peg 716. The peg 716 can engage the ribs 706. By engaging the ribs 706, the peg 716 can allow the receiving chamber 106 to be rotated without rotating the piston 112.

Rotation of the receiving chamber 106 without rotation of the piston 112 can allow the protrusions 312 to disengage from the notches 718. With the protrusions 312 disengaged from the notches 718, the receiving chamber 106 can be removed from the mixing chamber 104. As described above, removal of the receiving chamber 106 can allow the piston 112 to move and valve 302 to close thereby sealing the mixing chamber 104. The piston 112 can also include a recess 720. As shown in FIGS. 3A-3C, the recess 720 can allow the valve 302 and the filter 114 to rest within the piston 112. The piston 112 can also include one or more grooves 722. The grooves 722 can allow the O-rings or other sealing devices (not shown) to be installed to seal the interface between the piston 112 and an inner surface of the mixing chamber 104 while still allowing the piston 112 to move. Movement of the piston 112 towards the cap 116 can force the bone cement from the mixing chamber 104.

The piston 112 can be manufactured from metals, polymers, ceramics, or combinations thereof. The piston 112 can be manufactured from a variety of manufacturing techniques including, but not limited to, machining and injection molding.

Figure 8:
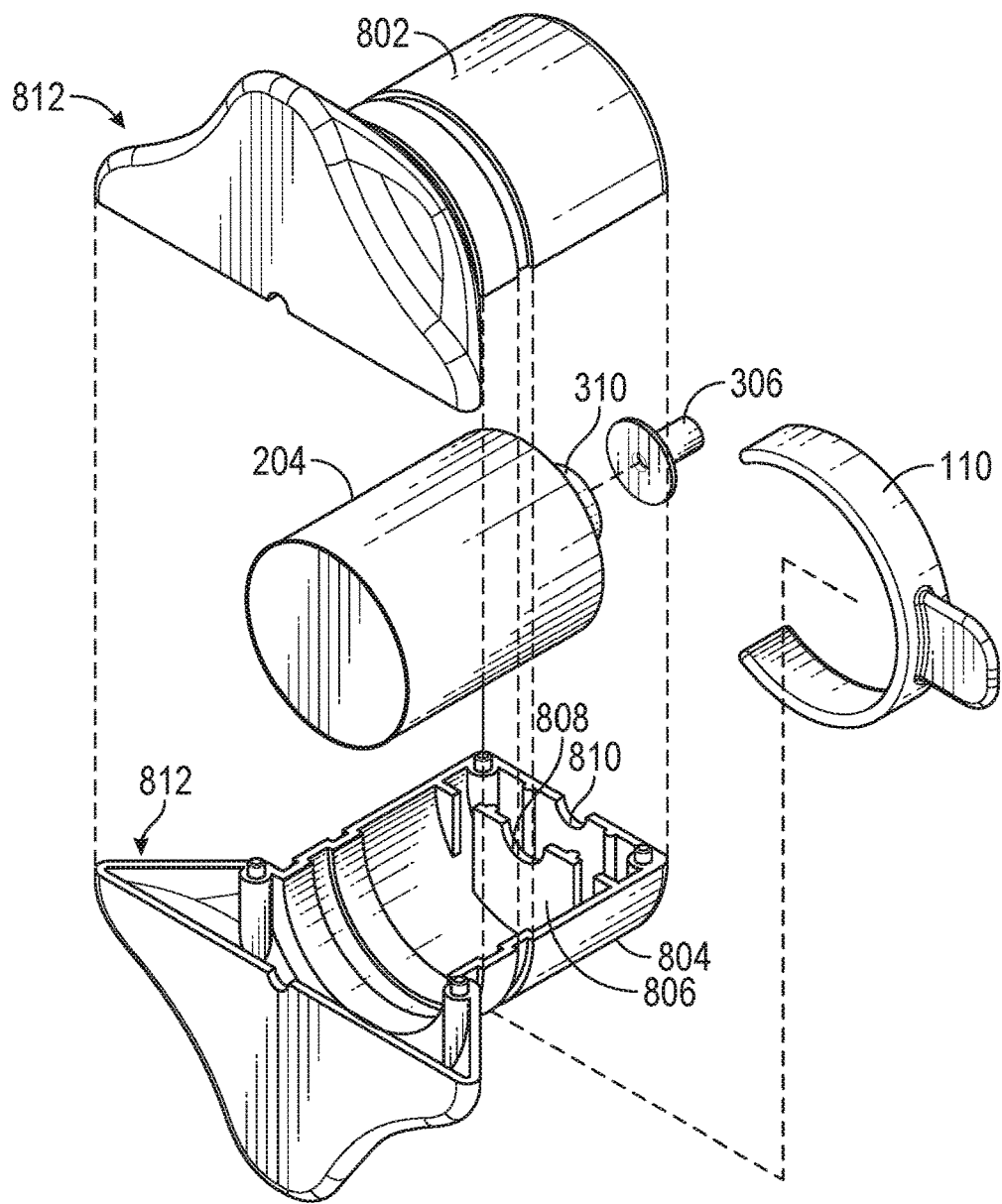
FIG. 8 shows an example exploded assembly of a base in accordance with at least one example of the present disclosure.

FIG. 8 shows an example exploded assembly of the base 108 in accordance with at least one example of the present disclosure. As shown in FIG. 8, the base 108 can include a first half 802 and a second half 804. The first half 802 and the second half 804 can each include a flange 806 (shown only on second half 804). The flanges 806 can include a first recess 808 that can be used to grip the head 310 of the bladder 204. In addition, the first half 802 and the second half 804 can each include a second recess 810 that can allow the seal 306 to pass from an interior portion of the base 108 to an exterior portion of the base 108 (see also FIGS. 3A-3C). The first half 802 and the second half 804 can snap together to enclose the bladder 204 and a portion of the seal 306.

Figure 9:
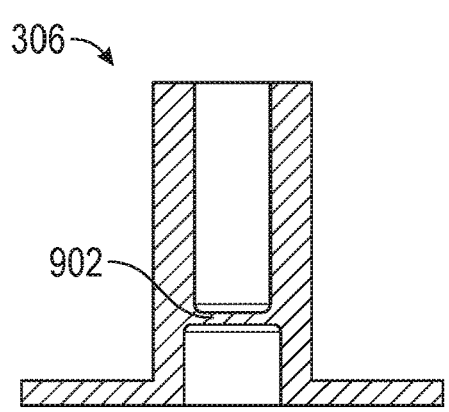
FIG. 9 shows an example cross section of a seal in accordance with at least one example of the present disclosure.

As shown in FIGS. 3A-3C, the seal 306 can rest against the head 310 of the bladder 204 to provide a seal such that once the bladder 204 is punctured, the second component of the bone cement is forced through the seal and does not leak into the interior portion of the base 108. In addition, the seal 306 can prevent air from entering the mixing chamber 104. Stated another way, the seal 306 helps maintain the vacuum created in the mixing chamber 104 and the valve assembly 202 when the bladder 204 is punctured. As shown in FIG. 9, the seal 306 can include a membrane 902 that can be punctured by the cannula 304 when the base 108 is inserted into the receiving chamber 106.

The base 108 can be manufactured from metals, polymers, ceramics, or combinations thereof. The base 108 can be manufactured from a variety of manufacturing techniques including, but not limited to, machining, injection molding, over molding, etc. For example, the base 108 can be injection molded from a polymer and then snapped together around the bladder 204 and the seal 306.

The safety strip 110 can be a flexible member that slips around a portion of the base 108. For example, the safety strip 110 can partially surround the base 108 and rest between the receiving chamber 106 and a portion of the base 108, such as flared portions 812 to hinder movement of the base 108. The safety strip 110 can also act as a tamper detection device. For example, the safety strip 110 can be formed such that removal of the safety strip 110 would result in inelastic deformation of the safety strip 110. As such, removal and replacement of the safety strip 110 would be evident to the surgeon or others upon visual inspection.

The safety strip 110 can be manufactured from metals, polymers, ceramics, or combinations thereof. The safety strip 110 can be manufactured from a variety of manufacturing techniques including, but not limited to, machining, injection molding, over molding, stamping, etc.

Figure 10:
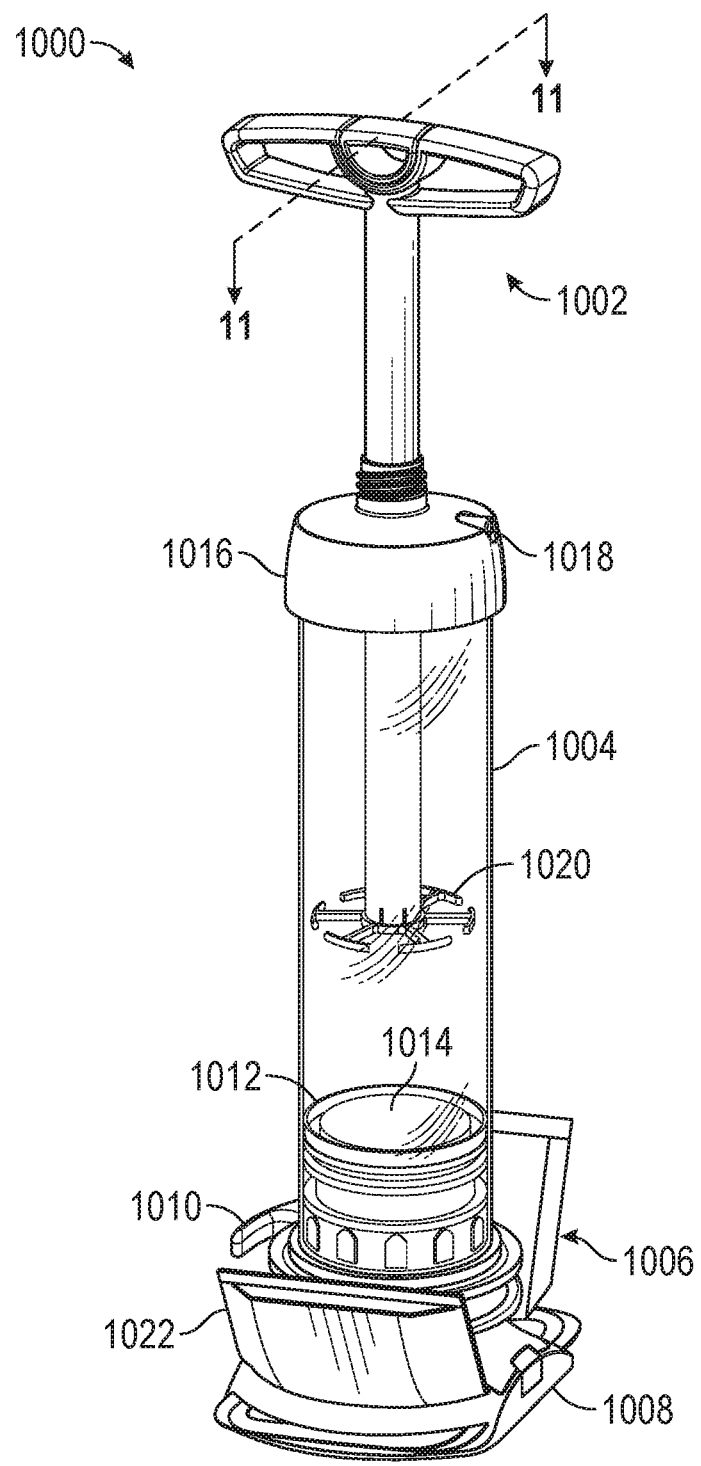
FIG. 10 shows an example system for mixing bone cement in accordance with at least one example of the present disclosure.

FIG. 10 shows an apparatus 1000 for mixing bone cement in accordance with at least one example of the present disclosure. As shown in FIG. 10, the apparatus 1000 can include a handle 1002, a mixing chamber 1004, a receiving chamber 1006, a base 1008, and a safety strip 1010. A piston 1012 can be located within the mixing chamber 1004 and a filter 1014 can be located on top of the piston 1012. The handle 1002 can pass through a cap 1016 that can seal a portion of the mixing chamber 1004. As discussed herein, the cap 1016 can include a vacuum port 1018 that can be used to connect the apparatus 1000 to a vacuum pump (not shown) to create a vacuum within the mixing chamber 1004.

The handle 1002 can be connected to a mixer 1020. After bone cement components have been introduced into the mixing chamber 1004, the handle 1002 can be articulated such that the mixer 1020 moves along a longitudinal axis of the mixing chamber 1004. The movement of the mixer 1020 can allow the bone cement components to be mixed such that a homogenous mixture is created.

A pouch 1022 can be located partially within and extend from the base 1008. The pouch 1022 can house a monomer or other liquid material that can mix with a powder or other liquid located within the mixing chamber 1004. The mixing of a first component (e.g., the powder) with the second component (e.g., the monomer) can create the bone cement. The apparatus 1000 can include one pouch or multiple pouches. Each of the pouches can include the same material or differing materials. For example, a first pouch can include a first liquid and a second pouch can include a second liquid that is different from the first liquid.

The walls defining the mixing chamber 1004 can be opaque or transparent. Transparent walls, such as shown in FIG. 10 can allow the surgeon to view the bone cement during a mixing process. By allowing the surgeon to view the bone cement, the surgeon can determine when the bone cement components have been thoroughly mixed. In addition, the surgeon can determine an amount of bone cement remaining in the mixing chamber 1004. For example, once the mixing chamber 1004 has been transferred to an applicator (not shown), the surgeon can utilize a transparent mixing chamber 1004 to determine if he or she has enough bone cement for a procedure to be undertaken. For instance, after installing a tibial component of a knee implant, the surgeon can view a remaining amount of bone cement in the mixing chamber 1004 to determine if he or she has enough bone cement remaining to install a femoral component of the knee implant or if more bone cement needs to be mixed.

Figure 11:
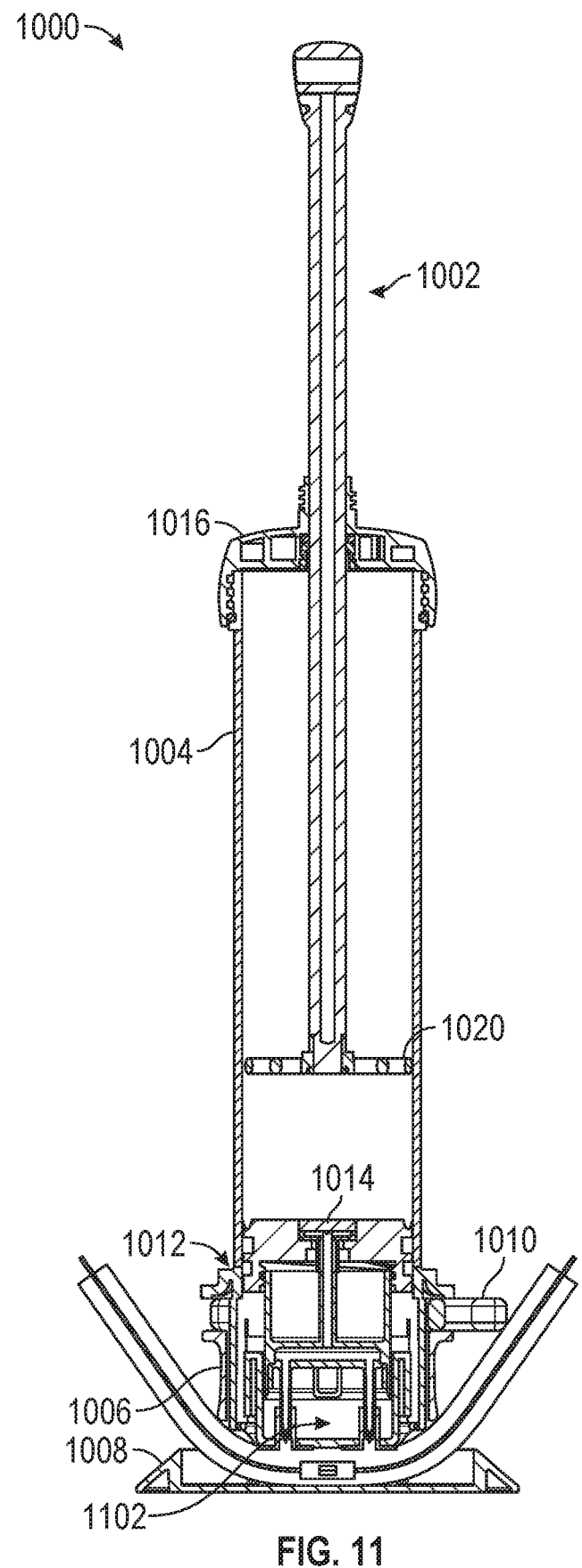
FIG. 11 shows an example of a cross-section of the system for mixing bone cement in accordance with at least one example of the present disclosure.
Figure 12:
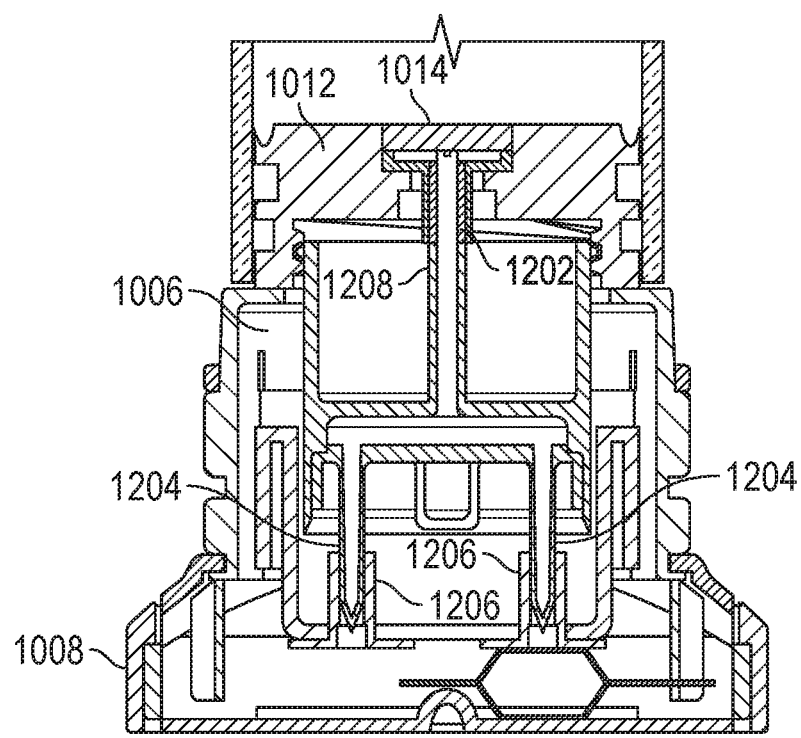
FIG. 12 shows a detail of a valve assembly in accordance with at least one example of the present disclosure.

FIG. 11 shows a cross section of the apparatus 1000 in accordance with at least one example of the present disclosure. As shown in FIG. 11, the apparatus 1000 can include a valve assembly 1102. FIG. 12 shows the valve assembly 1102 in accordance with at least one example of the present disclosure in greater detail. As shown in FIG. 12, the valve assembly 1102 can include the piston 1012, the filter 1014, a valve 1202, cannulas 1204, and seals 1206. The receiving chamber 1006 can define a conduit 1208 that can allow fluid communication between an interior portion of the receiving chamber 1006 and the mixing chamber 1004. The valve 1202 can be similar to the valve 302 described above with respect to FIGS. 5A and 5B.

As shown in FIGS. 10-12, the apparatus 1000 can be shipped with the base 1008 partially inserted within the receiving chamber 1006. The safety strip 1010 can hinder movement of the base 1008 relative to the receiving chamber 1006. Just as with FIGS. 3A-3C, the safety strip 1010 can be removed and movement of the base 1008 can allow the cannulas 1204 to puncture the pouch 1022 and allow the contents of the pouch 1022 to flow into the mixing chamber as described above with respect to the method 400 shown above in FIG. 4.

Figure 13:
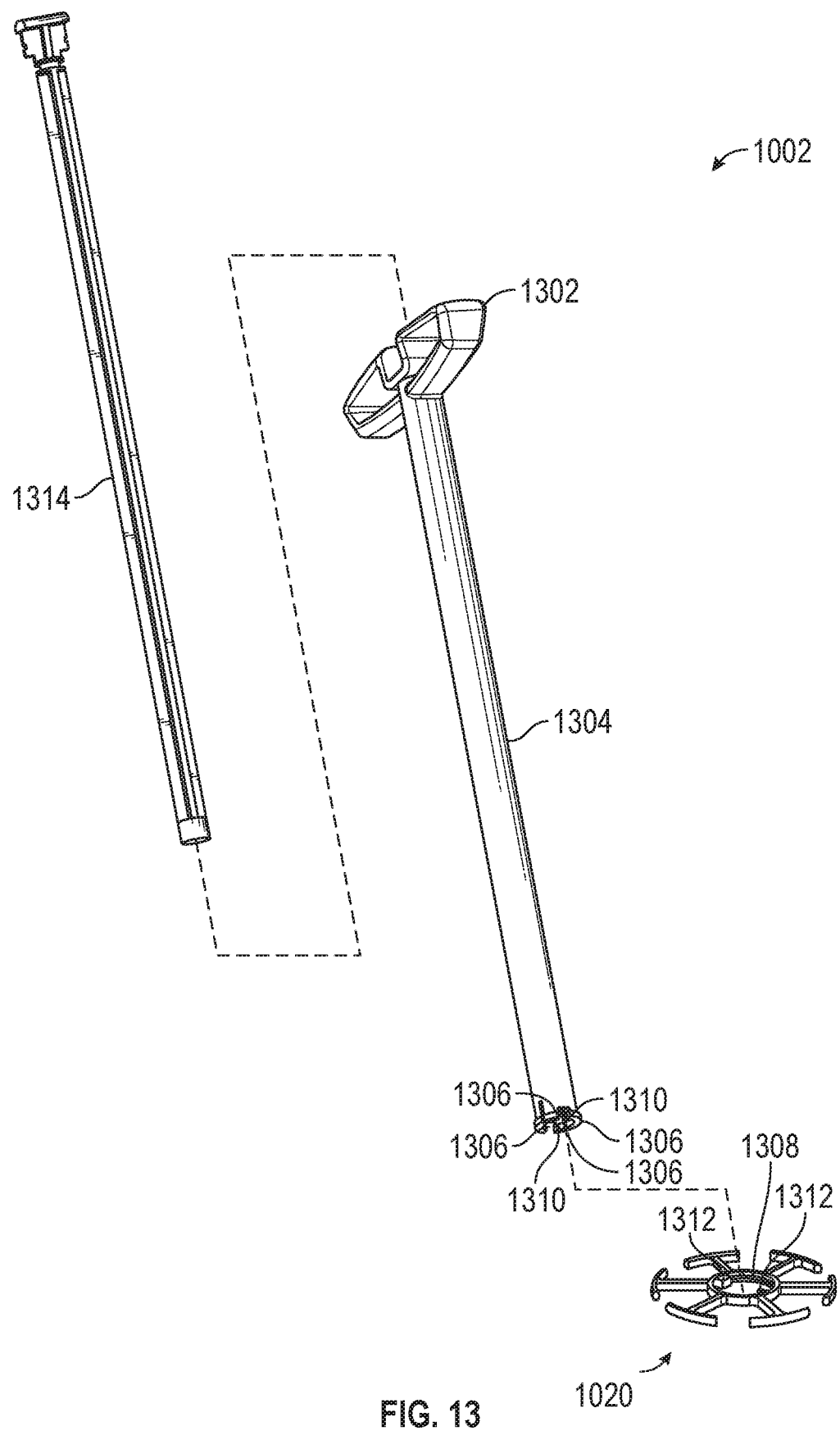
FIG. 13 shows an example exploded assembly of a handle and a mixer in accordance with at least one example of the present disclosure.

FIG. 13 shows an example exploded assembly of the handle 1002 and the mixer 1020. As shown in FIG. 13, the handle 1002 can include a grip 1302 and a cannulated rod 1304. The cannulated rod 1304 can include one or more flexible fingers 1306 that can engage an inner surface 1308 of the mixer 1020. In addition, the cannulated rod 1304 can define one or more notches 1310 that can engage one or more protrusions 1312 extending from the inner surface 1308.

The mixer 1020 can be attached to the cannulated rod 1304 by pressing the mixer 1020 onto the flexible finger 1306. Once the mixer 1020 is attached to the cannulated rod 1304, an inner rod 1314 can be inserted into the cannulated rod 1304. The inner rod 1314 can include a solid portion 1316 that can rest against the flexible fingers 1306. Once inserted, the solid portion 1316 can prevent the flexible fingers from flexing inward, thus securing the mixer 1020 to the cannulated rod 1304.

The grip 1302, the cannulated rod 1304, the inner rod 1314, and the mixer 1020 can be manufactured from polymers, metals, ceramics, or combinations thereof. For example, the grip 1302, the cannulated rod 1304, and the mixer 1020 can be manufactured from a surgical grad stainless steel or titanium and the inner rod 1314 can be manufactured from a polymer. The grip 1302, the cannulated rod 1304, the inner rod 1314, and the mixer 1020 can be manufactured from a variety of manufacturing techniques that include, but are not limited to, injection molding, over molding, machining, casting etc. For example, the cannulated rod 1304 and the mixer 1020 can each be machined using a computer numerical controlled (CNC) mill and the grip 1302 can be overmolded to a portion of the cannulated rod 1304.

Just as discussed above with respect to FIG. 7, the mixing chamber 1004 can include threads located at a first end of the mixing chamber 1004. The threads can cooperate with threads located on the cap 1016 such that the cap 1016 can be screwed to the mixing chamber 1004. The mixing chamber 1004 can also include ribs. As described herein, the ribs can be used to secure and rotate the piston 1012 via the receiving chamber 1006 and for mounting the mixing chamber 1004 to an applicator (not shown).

As discussed herein, the mixing chamber 1004 can be opaque or transparent. The mixing 1004 chamber can be manufactured from polymers, metals, ceramics, or a combination thereof. For example, the mixing chamber 1004 can be manufactured from a biocompatible polymer or metal. For instance, the mixing chamber 1004 can be manufactured from titanium such that the mixing chamber 1004 can be sterilized for use with multiple patients. In addition, the mixing chamber 1004 can be manufactured from a variety of manufacturing techniques including, but not limited to, machining, injection molding, etc. For example, the mixing chamber 1004 can be injection molded from a transparent polymer.

As disclosed herein the cap 1016 can define a through hole that can allow the mixed bone cement to exit the mixing chamber 1004 and the cannulated rod 1304 and the inner rod 1314 to pass through the cap. For example, as disclosed herein the cannulated rod 1304 an be separated from the mixer 1020 and the cannulated rod 1304 can then be pulled through the through hole and removed from the mixing chamber as described above. The cap 1016 can also include threads that can allow a nozzle (not shown) to be connected to the cap 1016. The nozzle can be used by the surgeon to direct the bone cement.

The cap 1016 can be manufactured from polymers, metals, ceramics, or a combination thereof. For example, the cap 1016 can be manufactured from a biocompatible polymer or metal. For instance, the cap 1016 can be manufactured from titanium such that the cap 1016 can be sterilized for use with multiple patients. In addition, the cap 1016 can be manufactured from a variety of manufacturing techniques including, but not limited to, machining, injection molding, etc. For example, the cap 1016 can be injection molded from a polymer.

As disclosed above with respect to the cannula 304, the cannulas 1204 can each include a collar and a tip. The cannulas 1204 can be press fit into the receiving chamber 1006. The tip can be sharp such that the tip can puncture the pouch 1022 when the base 1008 is inserted into the receiving chamber 1006.

The cannulas 1204 can be manufactured from metals, polymers, ceramics, or combinations thereof. The cannulas 2304 can be manufactured from a variety of manufacturing techniques including, but not limited to, stamping, machining, and injection molding.

As detailed above with respect to FIG. 3A-3C, the receiving chamber 1006 can include one or more protrusions. The protrusions can engage the piston 1012 located in the mixing chamber 1004. In addition, as discussed herein, the protrusions can allow for the piston 1012 to be attached to the receiving chamber 1006.

The receiving chamber 1006 can be manufactured from metals, polymers, ceramics, or combinations thereof. The receiving chamber 1006 can be manufactured from a variety of manufacturing techniques including, but not limited to, stamping, machining, and injection molding, etc.

The piston 1012 can include notches similar to the notches 718 discussed above. The notches can engage the protrusions of the receiving chamber 1006. Connecting the piston 1012 to the receiving chamber 1006 can prevent the piston 1012 from moving while the apparatus 1000 is in transport or while the vacuum is created in the mixing chamber 1004. The piston 1012 can also include a peg similar to peg 716 described above. The peg can engage the ribs. By engaging the ribs, the peg can allow the receiving chamber 1006 to be rotated without rotating the piston 1012.

Rotation of the receiving chamber 1006 without rotation of the piston 1012 can allow the protrusions to disengage from the notches. With the protrusions disengaged from the notches, the receiving chamber 1006 can be removed from the mixing chamber 1004. As disclosed herein, removal of the receiving chamber 1006 can allow the piston 1012 to move due to the negative pressure created by the vacuum within the mixing chamber 1004 and the valve 1202 to close thereby sealing the mixing chamber 1004. The piston 1012 can also include a recess, can allow the valve 1202 and the filter 1014 to rest within the piston 1012. The piston 1012 can also include one or more grooves. The grooves can allow O-rings or other sealing devices to be installed to seal the interface between the piston 1012 and an inner surface of the mixing chamber 1004 while still allowing the piston 1012 to move. Movement of the piston 1012 towards the cap 1016 can force the bone cement from the mixing chamber 1004.

The piston 1012 can be manufactured from metals, polymers, ceramics, or combinations thereof. The piston 1012 can be manufactured from a variety of manufacturing techniques including, but not limited to, machining and injection molding.

Figure 14A:
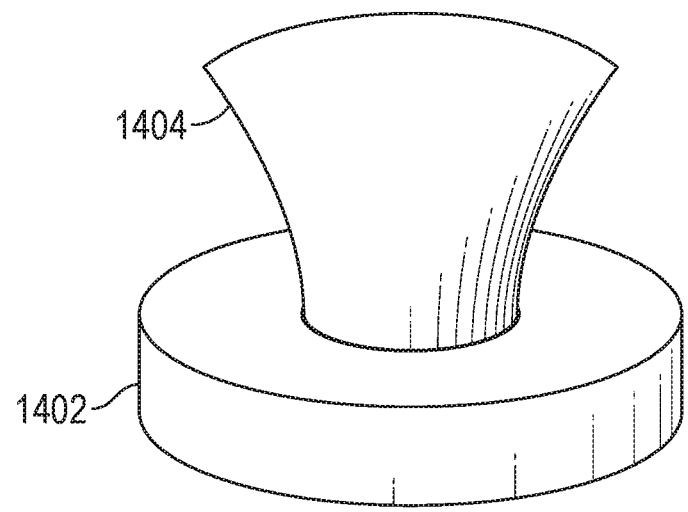
FIGS. 14A and 14B show an example valve in accordance with at least one example of the present disclosure.
Figure 14B:
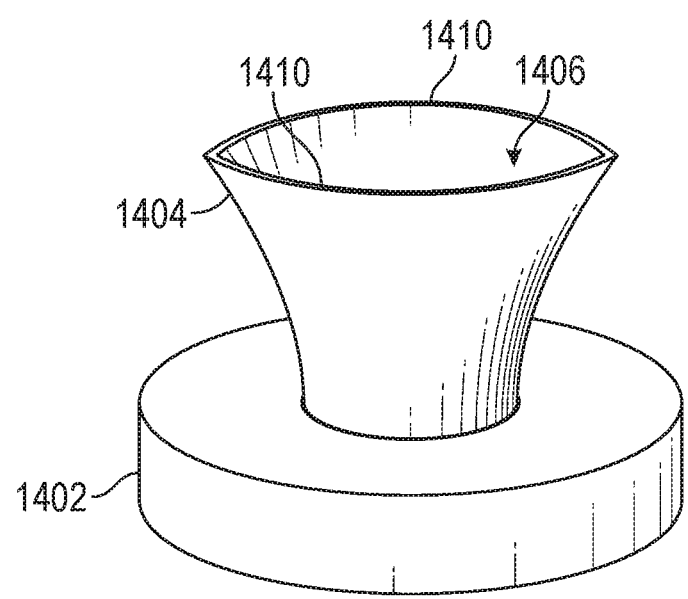

FIGS. 14A and 14B show the valve 1202. As shown in FIGS. 14A and 14B, the valve 1202 can include a base 1402 and a passage 1404. The passage 1404 can define an opening 1406. When the conduit 1208 passes through the opening 1406, the conduit 1208 can hold the opening 1406 open. When the conduit 1208 is removed from the passage 1404, the opening 1406, the edges 1410 of the opening 1406 can come together as shown in FIG. 14A to seal the opening 1406. The sealing of the opening 1406 can be cause by the vacuum within the mixing chamber 1004 and by the valve 1202 being formed of from a flexible impermeable polymer. For example, the valve 1202 can be formed from, for example, rubber or a polyethylene material such that when the edges 1410 contact one another they form an airtight seal.

Figure 15A:
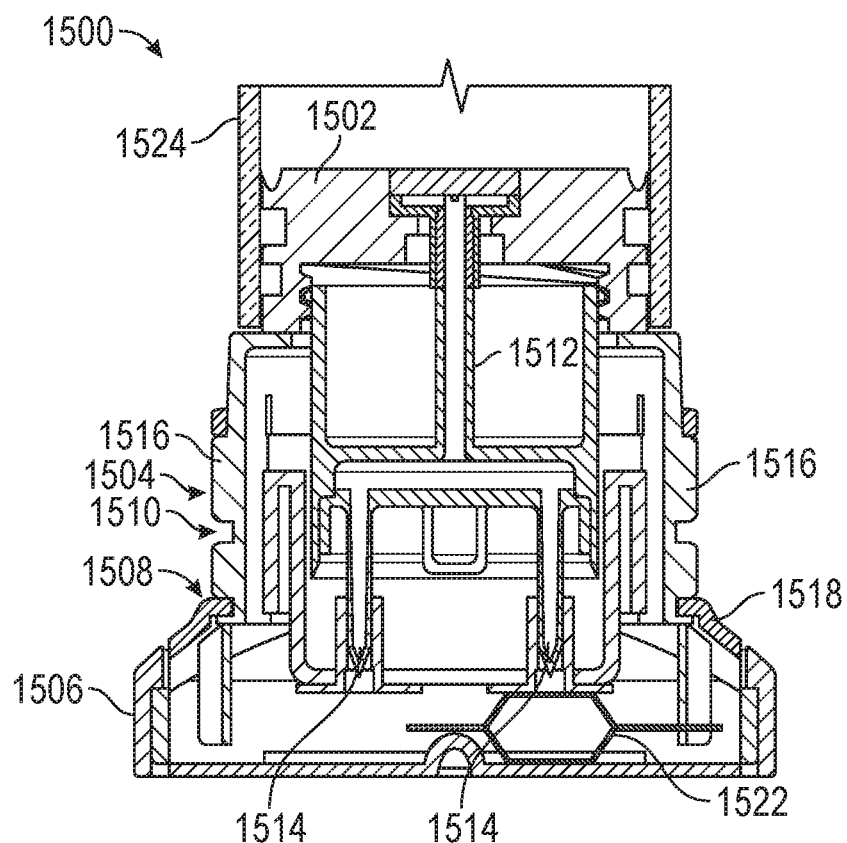
FIGS. 15A and 15B show an example receiving system in accordance with at least one example of the present disclosure.
Figure 15B:
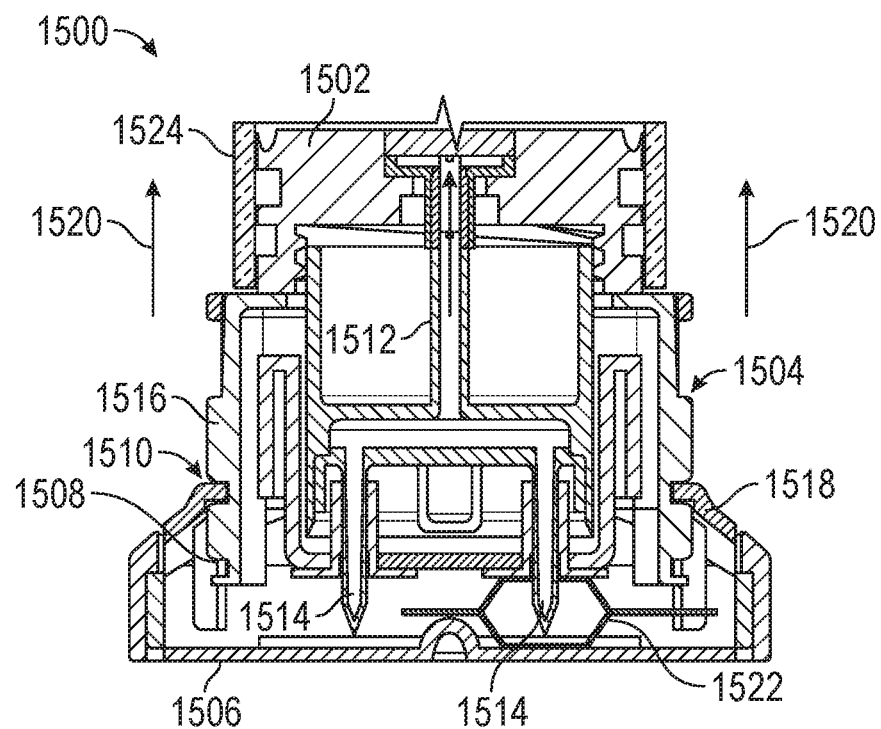

FIGS. 15A and 15B show a receiving system 1500 in accordance with at least one example of the present disclosure. The receiving system 1500 can include a piston 1502, a receiving chamber 1504, and a base 1506. The piston 1502 and the base 1506 can be any of the pistons and bases described herein. The receiving chamber 1504 can include components of any of the receiving chambers described herein. The receiving camber 1504 can also include a first indentation 1508 and a second indentation 1510. The receiving chamber 1504 can define a conduit 1512 and include cannulas 1514. The sidewall 1516 of the receiving chamber can be flexible. Thus, a user can press the sidewall 1516 such that a flange 1518 that can initially rest in the first indentation 1510 no longer rests within the first indentation 1510. When the flange 1518 is free of the first indentation 1510, the base 1506 can slide into the receiving chamber 1504 as depicted by arrows 1520. As the base 1506 slides into the receiving chamber 1504, the cannulas 1514 can puncture a pouch 1522 as shown in FIG. 15B, and thus allow the liquid within the pouch 1522 to flow through the cannulas 1514, the conduit 1512, and into the mixing chamber 1524.

The receiving chamber 1504 can be manufactured out of metals, polymers, or ceramics. In addition, the receiving chamber 1504 can be manufactured from a variety of manufacturing techniques including, but not limited to, injection molding, machining, overmolding, and the like. For example, the receiving chamber 1504 can be manufactured from a polymer via injection molding.

Figure 16:
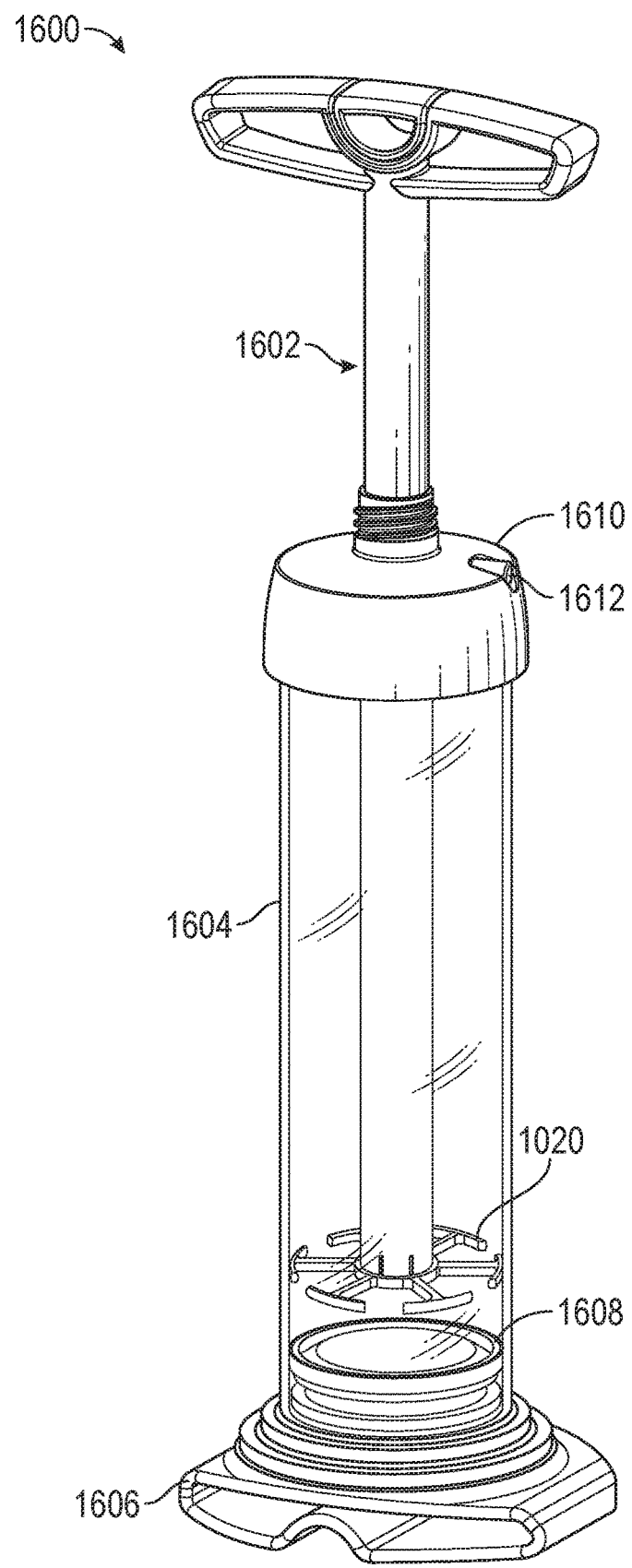
FIG. 16 shows an example system for mixing bone cement in accordance with at least one example of the present disclosure.

FIG. 16 shows an apparatus 1600 for mixing bone cement in accordance with at least one example of the present disclosure. As shown in FIG. 16, the apparatus 1600 can include a handle 1602, a mixing chamber 1604, and a base 1606. A piston 1608 can be located within the mixing chamber 1604. The handle 1602 can pass through a cap 1610 that can seal a portion of the mixing chamber 1604. As discussed herein, the cap 1610 can include a vacuum port 1612 that can be used to connect the apparatus 1600 to a vacuum pump (not shown) to create a vacuum within the mixing chamber 1604.

Prior to creating the vacuum within the mixing chamber 1604, the components of the bone cement can be placed in the mixing chamber 1604. Once the components of the bone cement are in the mixing chamber 1604 the cap 1610 can be placed on the mixing chamber 1604 to seal the mixing chamber 1604. The handle 1602 can then be used to mix the components of the bone cement. Once the bone cement has been mixed, the handle 1602, which can be similar to the handle 1602 shown in FIG. 13, can be removed from the apparatus 1600 by separating the mixer 1020 from the cannulated rod 1304 by removing the inner rod 1314 from the cannulated rod 1304 and the pulling the cannulated rod 1304 through the cap 1016 as described above. Once the cannulated rod 1304 and the inner rod 1314 have been removed from the cap 1026, a nozzle can be connected to the cap 1610 as disclosed herein.

Figure 17A:
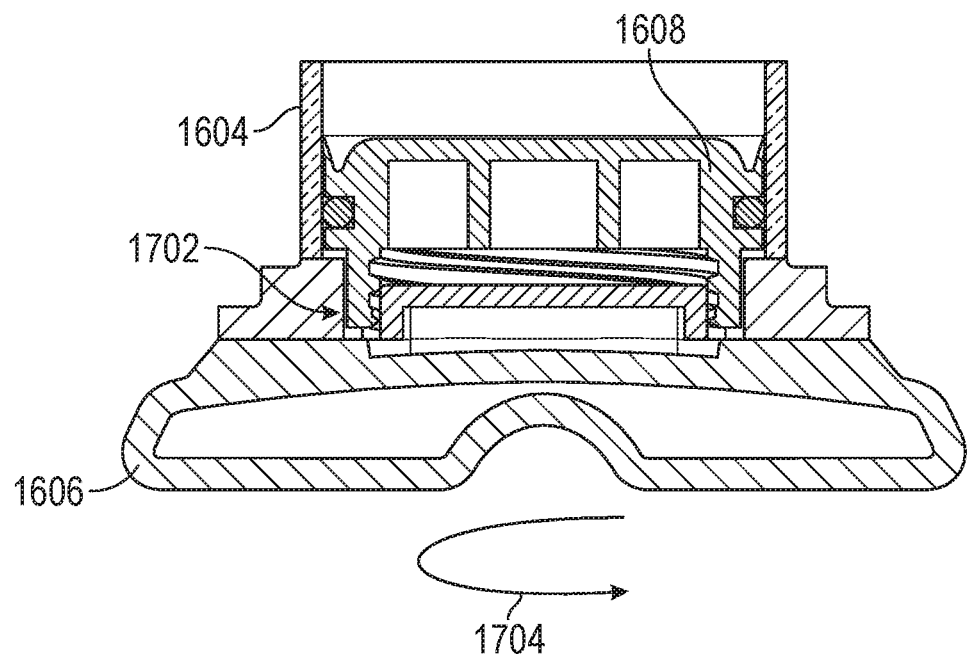
FIGS. 17A and 17B shows an example of a base in accordance with at least one example of the present disclosure.
Figure 17B:
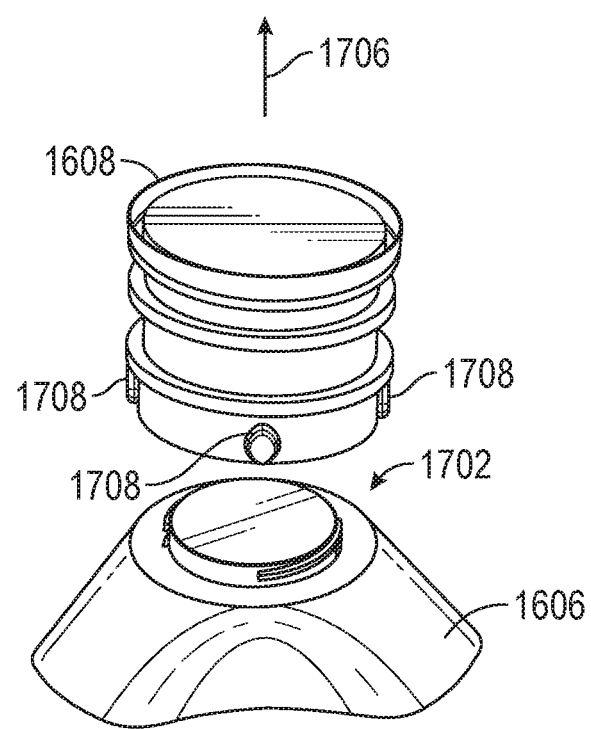

As shown in FIG. 17, the base 1606 can be connected to the piston 1608 via a threaded section 1702. Once the bone cement has been mixed, the base 1606 can be unscrewed from the piston 1608 as indicated by arrow 1704. The vacuum created via the vacuum port 1612 can cause the piston 1608 to travel towards the cap 1610 as indicated by arrow 1706. As shown in FIGS. 17A and 17B, the piston 1608 can include one or more protrusions 1708. The protrusions 1708 can engage one or more grooves in the mixing chamber 1604 as disclosed herein to prevent the piston 1608 from rotating as the base 1606 rotates.

Figure 18:
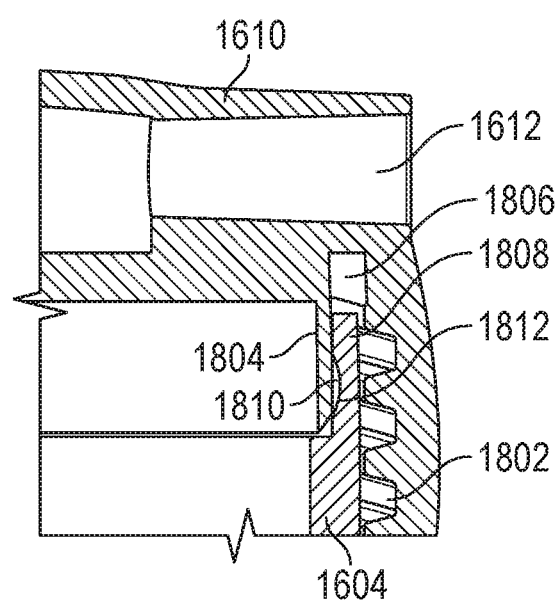
FIG. 18 shows an example cross-section of a cap in accordance with at least one example of the present disclosure.

FIG. 18 shows an example cross-section of the cap 1610. The cap 1610 can be any cap disclosed herein. As shown in FIG. 18, the cap 1610 can include a threaded section 1802 and an extended portion 1804. The threaded section 1802 and the extended portion 1804 can define a recess 1806. As the cap 1610 is threaded onto the mixing chamber 1604, a rim 1808 of the mixing chamber 1604 can slid into the recess 1806. The extended portion 1804 can define a protrusion 1810 that can rest in an indentation 1812 defined by the rim 1808. The protrusion 1810 and the indentation 1812 can form an airtight seal, without the use of O-rings or other sealants, which can allow the vacuum to be form as well as prevent the bone cement from leaking from the mixing chamber 1604.

As disclosed herein, the cap 1610 can be manufactured from a polymer, metal, or ceramic. In addition, the cap 1610 can be manufactured via manufacturing methods includes, but not limited to, injection molding, overmolding, machining, and the like. For example, the cap 1610 can be made of a polymer via injection molding.

It will be readily understood to those skilled in the art that various other changes in the details, material, and arrangements of the parts and method stages which have been described and illustrated in order to explain the nature of the inventive subject matter may be made without departing from the principles and scope of the inventive subject matter as expressed in the subjoined claims.

What is claimed is:

1. An apparatus for mixing bone cement, the apparatus comprising:
    a receiving chamber defining a conduit;
    a mixing chamber in fluid communication with the receiving chamber, the mixing chamber configured to house a first component of the bone cement;
    a cannula located in the receiving chamber and in fluid communication with the conduit;
    a base including a bladder arranged to be punctured by the cannula, the bladder configured to house a second component of the bone cement, wherein upon puncturing of the bladder by the cannula the second component of the bone cement passes through the conduit and the cannula into the mixing chamber;
    a piston located within the mixing chamber, the piston configured to seal the mixing chamber upon movement of the piston from a first position relative to the conduit to a second position relative to the conduit and
    a mixing handle passing into the mixing chamber, the mixing handle comprising a grip, a mixing head located within the mixing chamber, and a rod located along a central axis of the mixing chamber, the rod connecting the grip to the mixing head.

2. The apparatus of claim 1, further comprising a valve in fluid communication with the conduit, wherein the movement of the piston from the first position to the second position causes the valve to close.

3. The apparatus of claim 1, further comprising a safety strip connected to the base, the safety strip configured to prevent the bladder from being punctured by the cannula until the safety strip is removed from the base.

4. The apparatus of claim 1, wherein the base is configured to move relative to the mixing chamber co-axially.

5. The apparatus of claim 1, wherein the first component comprises a powder and the second component comprises a liquid.

6. The apparatus of claim 1, further comprising:
    a valve assembly in fluid communication with the bladder and the conduit; and
    a filter connected to the piston and configured to prevent the first component from entering the valve assembly and the bladder upon puncturing of the bladder.

7. The apparatus of claim 1, wherein the bladder includes a flexible membrane configured to decrease in volume upon puncturing of the bladder.

8. The apparatus of claim 1, wherein the base includes a second cannula and a second bladder, the second cannula arranged to puncture the second bladder.

9. The apparatus of claim 1, wherein the base further includes a flexible tab, when the flexible tab is in a first position, the base is secured to the mixing chamber in a fixed position, when the flexible tab is in a second position, the base is free to move along a longitudinal axis of the mixing chamber.

10. The apparatus of claim 1, wherein the bladder is completely located within the base.

11. The apparatus of claim 1, wherein a first portion of the bladder is located within an interior cavity defined by the base and a second portion of the bladder is located proximate an exterior of the base.

12. The apparatus of claim 1, further comprising a cap connected to the mixing chamber, the cap defining a vacuum port.

13. An apparatus for mixing bone cement, the apparatus comprising:
    a mixing chamber configured to house a first component of the bone cement;
    a receiving chamber defining a conduit configured to fluidly connect the mixing chamber and the receiving chamber;
    a cannula located within the receiving chamber and in fluid communication with the conduit;
    a base including a bladder configured to house a second component of the bone cement; a portion of the base sized to be received within the receiving chamber such that upon a relative movement between the base and the receiving chamber, the bladder is punctured by the cannula;
    a piston located within the mixing chamber and configured to engage the receiving chamber, the piston including a valve configured to allow the second component of the bone cement to pass through the cannula from the bladder into the mixing chamber and seal the mixing chamber upon disengagement of the receiving chamber from the piston; and
    a mixing handle passing into the mixing chamber, the mixing handle comprising a grip, a mixing head located within the mixing chamber, and a rod located along a central axis of the mixing chamber, the rod connecting the grip to the mixing head.

14. The apparatus of claim 13, further comprising a filter connected to the piston and configured to prevent the first component from entering the valve assembly and the bladder upon the bladder being punctured by the cannula.

15. The apparatus of claim 13, further comprising a safety strip connected to the base, the safety strip configured to prevent the bladder from being punctured by the cannula.

16. The apparatus of claim 13, wherein the relative movement between the base and the receiving chamber includes the base configured to move co-axially relative to the mixing chamber.

17. An apparatus for mixing bone cement, the apparatus comprising:
    a mixing chamber configured to house a first component of the bone cement;
    a cap connected to a first end of the mixing chamber and defining a through hole along a central axis of the cap and mixing chamber;
    a receiving chamber defining a conduit configured to fluidly connect the mixing charrrber and the receiving chamber;
    a cannula located within the receiving chamber and in fluid communication with the conduit;
    a base including a bladder configured to house a second component of the bone cement, a portion of the base sized to be received within the receiving chamber such that upon a relative movement between the base and the receiving chamber, the bladder is punctured by the cannula;
    a piston located within the mixing chamber and configured to engage the receiving chamber, the piston including a valve configured to allow the second component of the bone cement to pass through the cannula from the bladder into the mixing chamber and seal the mixing chamber upon disengagement of the receiving chamber from the piston; and a mixing handle comprising a grip, a mixing head located within the mixing chamber, and a rod, the rod oriented along the central axis of the cap and the mixing chamber passing through the through hole in the cap, the rod connecting the grip to the mixing head.

18. The apparatus of claim 17, wherein the base is connected to the piston via a threaded connection.

19. The apparatus of claim 17, wherein the cannulation component includes a plurality of flexible tabs configured to engage the mixing head.

* * * * *

UNITED STATES PATENT AND TRADEMARK OFFICE
CERTIFICATE OF CORRECTION

PATENT NO. : 10,905,485 B2  
APPLICATION NO. : 15/660177  
DATED : February 2, 2021  
INVENTOR(S) : Giffard et al.

Page 1 of 1

It is certified that error appears in the above-identified patent and that said Letters Patent is hereby corrected as shown below:

In the Claims

In Column 16, Line 18, in Claim 13, delete "cement;" and insert --cement,-- therefor In Column 16, Line 54, in Claim 17, delete "charrrber" and insert --chamber-- therefor Signed and Sealed this  
Twentieth Day of April, 2021

Drew Hirshfeld  
*Performing the Functions and Duties of the*  
*Under Secretary of Commerce for Intellectual Property and*  
*Director of the United States Patent and Trademark Office*